（12） United States Patent
Murai

(10) Patent No.: US 11,806,293 B2
(45) Date of Patent: Nov. 7, 2023

(54) BED SYSTEM

(71) Applicant: PARAMOUNT BED CO., LTD., Tokyo (JP)

(72) Inventor: Shinya Murai, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 42 days.

(21) Appl. No.: 17/363,773

(22) Filed: Jun. 30, 2021

(65) Prior Publication Data

US 2021/0338503 A1 Nov. 4, 2021

Related U.S. Application Data

(63) Continuation of application No. 16/343,875, filed as application No. PCT/JP2018/013104 on Mar. 29, 2018, now Pat. No. 11,083,654.

(30) Foreign Application Priority Data

Apr. 28, 2017 (JP) ................................. 2017-090435

(51) Int. Cl.
*A61B 5/00* (2006.01)
*A61B 5/02* (2006.01)
(Continued)

(52) U.S. Cl.
CPC ................. *A61G 7/05* (2013.01); *A61B 5/00* (2013.01); *A61B 5/0046* (2013.01); *A61B 5/02* (2013.01);
(Continued)

(58) Field of Classification Search
CPC ...... A61G 7/05; A61G 7/0527; A61B 5/0046; A61B 5/02; A61B 5/11; A61B 5/68;
(Continued)

(56) References Cited

U.S. PATENT DOCUMENTS

| 2009/0227882 A1 | 9/2009 | Foo | |
|---|---|---|---|
| 2009/0237264 A1 | 9/2009 | Bobey | |
| 2011/0205062 A1* | 8/2011 | Pesot | A61B 5/0006 340/286.07 |
| 2011/0210925 A1* | 9/2011 | Pittenger | G16H 40/67 715/761 |

(Continued)

FOREIGN PATENT DOCUMENTS

| JP | 2005-237667 | 9/2005 |
|---|---|---|
| JP | 2006-239084 | 9/2006 |

(Continued)

OTHER PUBLICATIONS

International Search Report dated May 22, 2018 in International (PCT) Application No. PCT/JP2018/013104.

*Primary Examiner* — Carl H Layno
*Assistant Examiner* — Anh-Khoa N Dinh
(74) *Attorney, Agent, or Firm* — Wenderoth, Lind & Ponack, L.L.P.

(57) ABSTRACT

A bed system including an acquisition unit and a display, in which the acquisition unit acquires user interface device information from a plurality of user interface devices and the display displays a plurality of images corresponding respectively to the plurality of user interface devices on a single screen based on the user interface device information. One set of the plurality of user interface device information includes state information including at least one of bed state information relating to the state of one bed among a plurality of beds and user state information relating to the state of a user of the one bed among the plurality of beds. One image among the plurality of images includes a state display corresponding to the state information. When the state information is abnormal, the first display displays a warning display on the one image among the plurality of images.

13 Claims, 22 Drawing Sheets

(51) Int. Cl.
*A61B 5/11* (2006.01)
*A61G 7/05* (2006.01)
*G06F 3/0481* (2022.01)

(52) U.S. Cl.
CPC .............. *A61B 5/11* (2013.01); *A61B 5/68* (2013.01); *A61B 5/70* (2013.01); *G06F 3/0481* (2013.01); *A61G 7/0527* (2016.11)

(58) Field of Classification Search
CPC .. A61B 5/70; A61B 5/00; A61B 5/742; A61B 5/744; A61B 5/743; A61B 5/1115; A61B 5/021; A61B 5/024; A61B 5/0816; A61B 5/14532; A61B 5/4806; A61B 5/6891; A61B 5/02055; A61B 5/746; A61B 5/14542; G06F 3/0481; G06F 3/04817; G06F 3/04842; G06F 3/0488; G06F 3/04847; G06F 3/0489; G06F 3/0482; G16H 40/63; G16H 40/20; G16H 10/60; G16H 40/67; G16Z 99/00

See application file for complete search history.

(56) References Cited

U.S. PATENT DOCUMENTS

| | | |
|---|---|---|
| 2012/0089419 A1* | 4/2012 | Uster ............... A61G 7/015 |
| | | 705/3 |
| 2014/0266733 A1 | 9/2014 | Hayes |
| 2014/0324451 A1 | 10/2014 | Pesot et al. |
| 2015/0164238 A1 | 6/2015 | Benson |
| 2015/0302150 A1* | 10/2015 | Mazar ............... G16H 40/63 |
| | | 705/2 |
| 2018/0146915 A1 | 5/2018 | Nemoto |
| 2018/0242918 A1 | 8/2018 | Kogure et al. |

FOREIGN PATENT DOCUMENTS

| | | |
|---|---|---|
| JP | 2009-528859 | 8/2009 |
| JP | 2012-86013 | 5/2012 |
| JP | 2015-191526 | 11/2015 |
| JP | 2016-202463 | 12/2016 |
| JP | 2017-047104 | 3/2017 |
| WO | 2016/042757 | 3/2016 |

* cited by examiner

BED SYSTEM

CROSS-REFERENCE TO RELATED APPLICATIONS

This application is a continuation of U.S. patent application Ser. No. 16/343,875, filed on Apr. 22, 2019, now U.S. Pat. No. 11,083,654 which issued on Aug. 10, 2021, which is a U.S. national stage application of the PCT International Application No. PCT/JP2018/013104 filed on Mar. 29, 2018, which claims the benefit of foreign priority of Japanese Patent Application No. 2017-090435, filed on Apr. 28, 2017.

TECHNICAL FIELD

An embodiment of the present invention relates to a bed system.

BACKGROUND ART

A hospital bed having a graphical user interface connected to a patient-holding structure for holding a patient is available (PTL 1). The graphical user interface is capable of displaying information relating to the patient.

A plurality of patients are typically cared for in a hospital, a care facility, or the like. Demand exists for a bed system that is easy to use and can be used with a plurality of patients.

CITATION LIST

Patent Literature

[PTL 1] Japanese Patent Application Publication No. 2012-86013

SUMMARY OF INVENTION

Technical Problem

An embodiment of the present invention provides a bed system having improved usability.

Solution to Problem

A bed system according to an embodiment includes an acquisition unit and a first display. The acquisition unit acquires a plurality of user interface device information from a plurality of user interface devices. The first display displays a plurality of images corresponding respectively to the plurality of user interface devices on a single screen on the basis of the plurality of user interface device information acquired by the acquisition unit. One set of the plurality of user interface device information includes state information including at least one of bed state information relating to the state of one bed among a plurality of beds and user state information relating to the state of a user of the one bed among the plurality of beds. One image among the plurality of images includes a state display corresponding to the state information. When the state information is abnormal, the first display displays a warning display on the one image among the plurality of images.

Advantageous Effects of Invention

An embodiment of the present invention can provide a bed system having improved usability.

DESCRIPTION OF EMBODIMENTS

Figure 1:
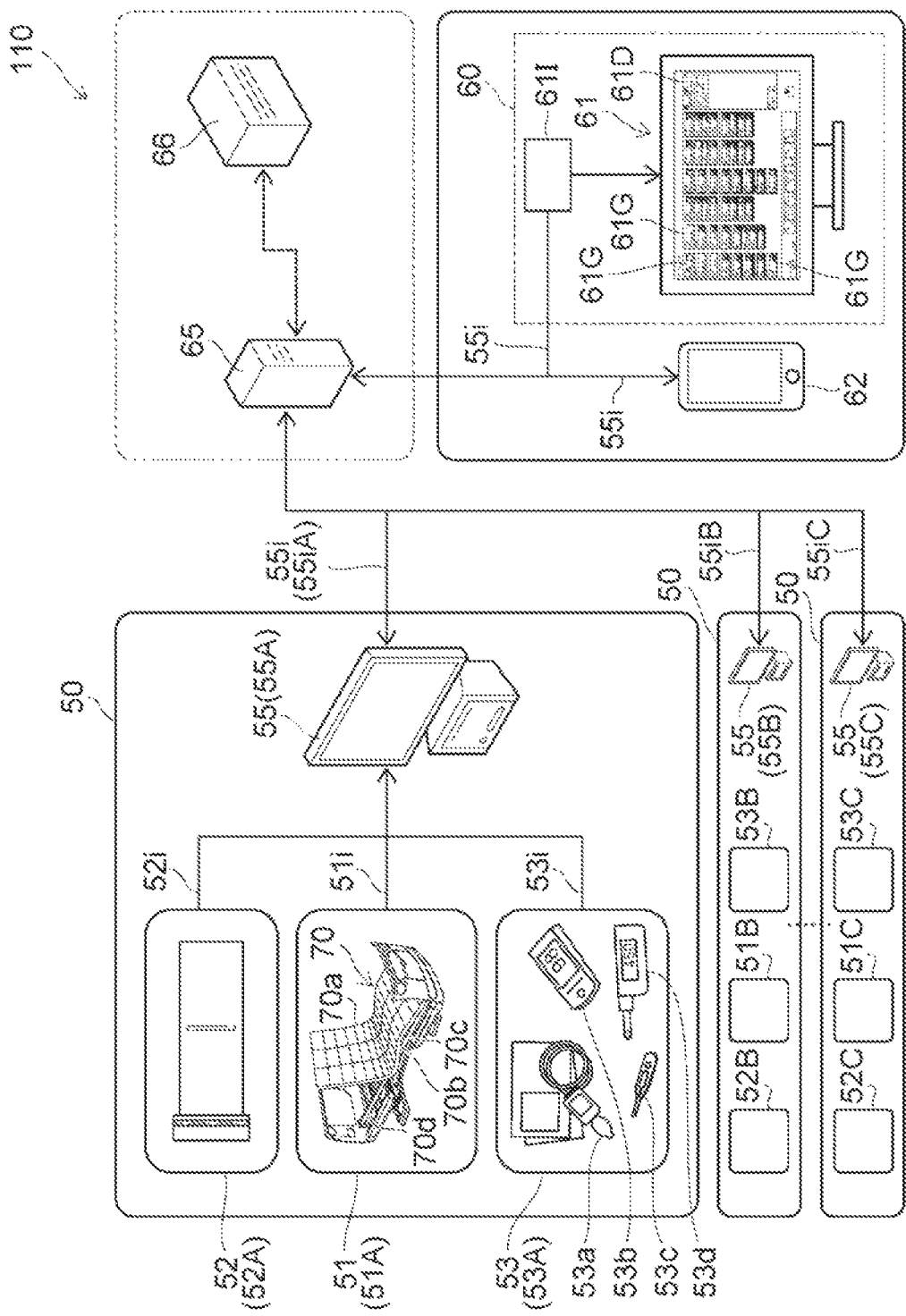
FIG. 1 is a pattern diagram showing an example of a bed system according to an embodiment.

Embodiments of the present invention will be described below with reference to the figures.

In the description and the figures, identical elements to those appearing in earlier figures have been allocated identical reference numerals, and where appropriate, detailed description thereof has been omitted.

FIG. 1 is a pattern diagram showing an example of a bed system according to an embodiment.

As shown in FIG. 1, a bed system 110 according to an embodiment includes an acquisition unit 61I and a first display 61. The acquisition unit 61I acquires a plurality of user interface device information 55i. The plurality of user interface device information 55i is acquired from a plurality of user interface devices 55.

The acquisition unit 61I and the first display 61 are included in a first input/output device 60. The first input/output device 60 is a master station device, for example. The first input/output device 60 is capable of communicating with a plurality of bed devices 50.

One bed device 50 among the plurality of bed devices 50 includes one user interface device 55 among the plurality of user interface devices 55. One bed device 50 among the plurality of bed devices 50 includes a bed 51 and the user interface device 55. The user interface device 55 is connected to the bed 51.

The plurality of user interface devices 55 include user interface devices 55A to 55C and so on, for example. The user interface devices 55A to 55C respectively output user interface device information 55iA to 55iC and so on. The plurality of user interface device information 55i (the user interface device information 55iA to 55iC and so on) is supplied to the acquisition unit 61I via a server 65 or the like, for example. The number of user interface devices constituting the plurality of user interface devices 55 is a desired integer no smaller than 2. The number of sets of user interface device information constituting the plurality of user interface device information 55i corresponds to the number of user interface devices constituting the plurality of user interface devices 55.

The acquisition unit 61I is a communication circuit, for example. The acquisition unit 61I includes an electric circuit, for example. The acquisition unit 61I and the plurality of user interface devices 55 exchange information (signals) by a wired or wireless method selected as desired.

The plurality of user interface device information 55i acquired from the plurality of user interface devices 55 may be supplied to an electronic medical record storage unit 66 or the like via the server 65, for example.

The plurality of user interface devices 55 (the user interface devices 55A to 55C and so on) are provided to correspond respectively to the plurality of beds 51 (beds 51A to 51C and so on).

The bed 51 includes a moving part 70, for example. The moving part 70 includes a back section 70a, a knee section 70b, a leg section 70c, a height modifying part 70d (a bed elevator, for example), and so on, for example. By operating the moving part 70, at least one of "back-raising", "knee-raising", "height adjustment", and "inclining" can be performed. "Inclining" includes at least one of rolling and tilting.

An actuator or the like, for example, moves the moving part 70. The moving part 70 may include a sensor (a load sensor, for example), for example. Information relating to the state of a user of the bed 51 may be acquired by detecting a load exerted on the actuator. The user is a patient, a care receiver, or the like, for example. For example, the load sensor or the like provided on the moving part 70 may output information relating to the user (at least one of sitting up, sitting on the edge of the bed, bed departure, and "monitoring", for example). "Monitoring" is a state in which the user remains out of bed continuously for a specified time, for example. When the user remains out of bed continuously for the specified time, the load sensor or the like outputs a signal (information) relating to "monitoring".

Bed moving part information 51i is supplied to the user interface device 55 from each of (one of) the plurality of beds 51. The bed moving part information 51i includes information relating to at least one of the height and the angle of one of the plurality of beds. The bed moving part information 51i includes whether or not the height of the bed 51 is at a minimum, for example. The bed moving part information 51i includes information relating to the angle of at least one of the back section 70a, the knee section 70b, and the leg section 70c, for example. The bed moving part information 51i may also include information relating to the angle of incline of the bed 51.

In this example, the bed 51 is provided with an auxiliary device 52. The auxiliary device 52 is a sheet (or a plate), for example. The auxiliary device 52 is provided between the section of the bed 51 and the mattress, for example. The auxiliary device 52 includes a sensor (at least one of a vibration sensor, a noise sensor, and a force sensor, or the like), for example. The vibration sensor includes an air pressure sensor (a pressure sensor, for example). The auxiliary device 52 is capable of detecting at least one of sleeping, waking up, sitting up, bed departure, monitoring, heart rate, and respiration rate in relation to the user, for example. The detection result is supplied to one of the plurality of user interface devices 55. For example, the sensor included in the auxiliary device 52 detects the user behavior state of the user. The user behavior state includes at least one of bed departure, sleeping, waking up (lying flat in bed), sitting up, and sitting on the edge of the bed in relation to the user of the bed 51. User behavior information 52i including information relating to the user behavior state is supplied to the plurality of user interface devices 55.

The bed 51 may acquire at least a part of the user behavior information 52i. When a sensor is provided in the actuator provided on the bed 51, as described above, the bed 51 may detect the user behavior state (a state including at least one of bed departure, sleeping, waking up, sitting up, and sitting on the edge of the bed). The bed 51 may be considered to include the auxiliary device 52.

In this example, measurement information 53i is also supplied to the user interface device 55. A measurement device 53 acquires the measurement information 53i. The measurement device 53 includes at least one of a blood pressure gauge 53a, a pulse oximeter 53b, a thermometer 53c, and a blood glucose meter 53d, for example. The measurement device 53 acquires information (vital signs information, for example) relating to at least one of the blood pressure, the blood oxygen saturation ($SpO_2$), the blood glucose level, and the body temperature of the user, for example. The blood oxygen saturation is the percutaneous arterial oxygen saturation, for example. The measurement device 53 supplies the vital signs information to the user interface device 55 by communicating with the user interface device 55, for example. This communication is performed by short-range wireless communication, for example. A nurse or the like may input at least a part of the vital signs information into the user interface device 55 manually.

For example, the user interface device 55A (one of the plurality of user interface devices 55) is associated with the bed 51A (one of the plurality of beds 51), an auxiliary device 52A (one of the plurality of auxiliary devices 52), and a measurement device 53A (one of the plurality of measurement devices 53). The user interface device 55B, for example, is associated with the bed 51B, an auxiliary device 52B, and a measurement device 53B. The user interface device 55C, for example, is associated with the bed 51C, an auxiliary device 52C, and a measurement device 53C.

The bed moving part information 51i, the user behavior information 52i, and the measurement information 53i, described above, are supplied to the acquisition unit 61I via the user interface device 55 as the user interface device information 55i.

In this example, at least a part of the user interface device information 55i is supplied to a second display 62. The second display 62 is a display of a mobile terminal, for example. A caregiver or the like, for example, uses the second display 62. The caregiver or the like provides the respective users of the plurality of beds with nursing care or medical care. For example, each of a plurality of caregivers or the like owns one second display 62.

At least one of the first display 61 and the second display 62 includes a display device (a liquid crystal display device, an EL display device, or the like, for example), for example. The size (the length of the diagonal of the screen, for example) of the first display 61 is greater than the size (the length of the diagonal of the screen, for example) of the second display 62. The acquisition unit 61I may be provided in a casing in which the first display 61 is provided.

Meanwhile, the plurality of caregivers or the like share the first display 61. The first display 61 is provided in a nurse station or the like, for example. The first display 61 is a display of a master station device, for example. The first display 61 is provided in a different position to the plurality of user interface devices 55. The first display 61 is provided in a location (a remote location) apart from the plurality of user interface devices 55. From the display on the first display 61 provided in a remote location, the caregivers or the like can ascertain the states of the beds 51 connected to the plurality of user interface devices 55 or the states of the users of the beds 51.

The first display 61 displays a plurality of images 61G on a single screen 61D on the basis of the plurality of user interface device information 55i acquired by the acquisition unit 61I. The plurality of images 61G correspond respectively to the plurality of user interface devices 55.

The single screen 61D displays the plurality of images 61G corresponding respectively to the plurality of user interface devices 55 side by side. The caregivers or the like can thus ascertain the states of the respective users of the plurality of beds 51 efficiently and in an easily understandable manner. As a result, a bed system having improved usability can be provided.

The plurality of beds 51 are provided in a hospital, a care facility, or the like, for example. The user interface devices 55 are provided respectively on the plurality of beds 51. One user interface device 55 can provide the caregiver or the like with information relating to the state of the bed 51 to which the user interface device 55 is connected and the state of the user of the bed 51. Meanwhile, in a nurse station located away from the bed 51, it is necessary to ascertain the states of the plurality of beds 51 and the plurality of users as a whole. By displaying the plurality of images 61G on the single screen 61D, the overall situation can be ascertained. As a result, high-priority measures can be implemented efficiently.

For example, the plurality of user interface device information 55i acquired from the plurality of user interface devices 55 is displayed at the same time on the single screen 61D of the first display 61. The plurality of images 61G are displayed collectively on the single screen 61D. As a result, the information can be ascertained more easily than in a case where, for example, the plurality of user interface devices 55 are accessed individually from the nurse station and information is acquired from each of the plurality of user interface devices 55.

According to an embodiment, information exchange (communication) is performed rapidly between a plurality of caregivers and the like, for example. Communication delays are suppressed. The productivity of the caregiver or the like improves. Risks to the users can be identified quickly.

As described above, one set of the plurality of user interface device information 55i includes state information. The state information includes at least one of the bed state information relating to the state of one bed 51 among the plurality of beds 51 and the user state information relating to the state of the user of the one bed 51 among the plurality of beds 51. The bed state information includes, for example, the bed moving part information relating to at least one of the height and the angle of the one bed 51 among the plurality of beds 51. The user state information includes at least one of the vital signs information relating to the user and the user behavior information relating to the user. The vital signs information includes information relating to at least one of the blood pressure, the blood oxygen saturation, the blood glucose level, the heart rate, the pulse rate, the respiration rate, the weight, and the body temperature of the user. The user behavior information includes information relating to at least one of bed departure, sleeping, waking up, sitting up, and sitting on the edge of the bed in relation to the user.

One image among the plurality of images 61G includes a state display (a pictogram, a color, or the like, to be described below) corresponding to the state information described above. As will be described below, when the state information is abnormal, the first display 61 displays a warning display on the one image among the plurality of images 61G.

In an embodiment, as will be described below, the plurality of state information (the bed moving part information 51i, the user behavior information 52i, the measurement information 53i, and so on) included in the user interface device information 55i is displayed as a single combination. As a result, the state information relating to the states of the plurality of beds 51 and the plurality of users can be displayed clearly on the single screen 61D. By employing a display of combined information, risks can be identified easily and efficiently. For example, signs indicating risk to a user (an injury, a deterioration of the medical condition, and so on) can easily be ascertained from the states of the plurality of beds 51 and the states of the plurality of users at an appropriate timing.

Hence, according to an embodiment, efficiently ascertaining the states of the plurality of beds 51 (states of devices) and the states of the plurality of users in a remote location can be achieved more easily. As a result, an improvement in usability can be achieved. For example, the quality of medical or nursing care can be improved.

A processing device such as a computer, for example, generates data relating to the screen 61D and the plurality of images 61G displayed on the first display 61. The processing device may be provided in the acquisition unit 61I or the first display 61, for example. The processing device may be provided in the server 65 or the like, for example.

Examples of displays displayed on the first display 61 will be described below.

Figure 2:
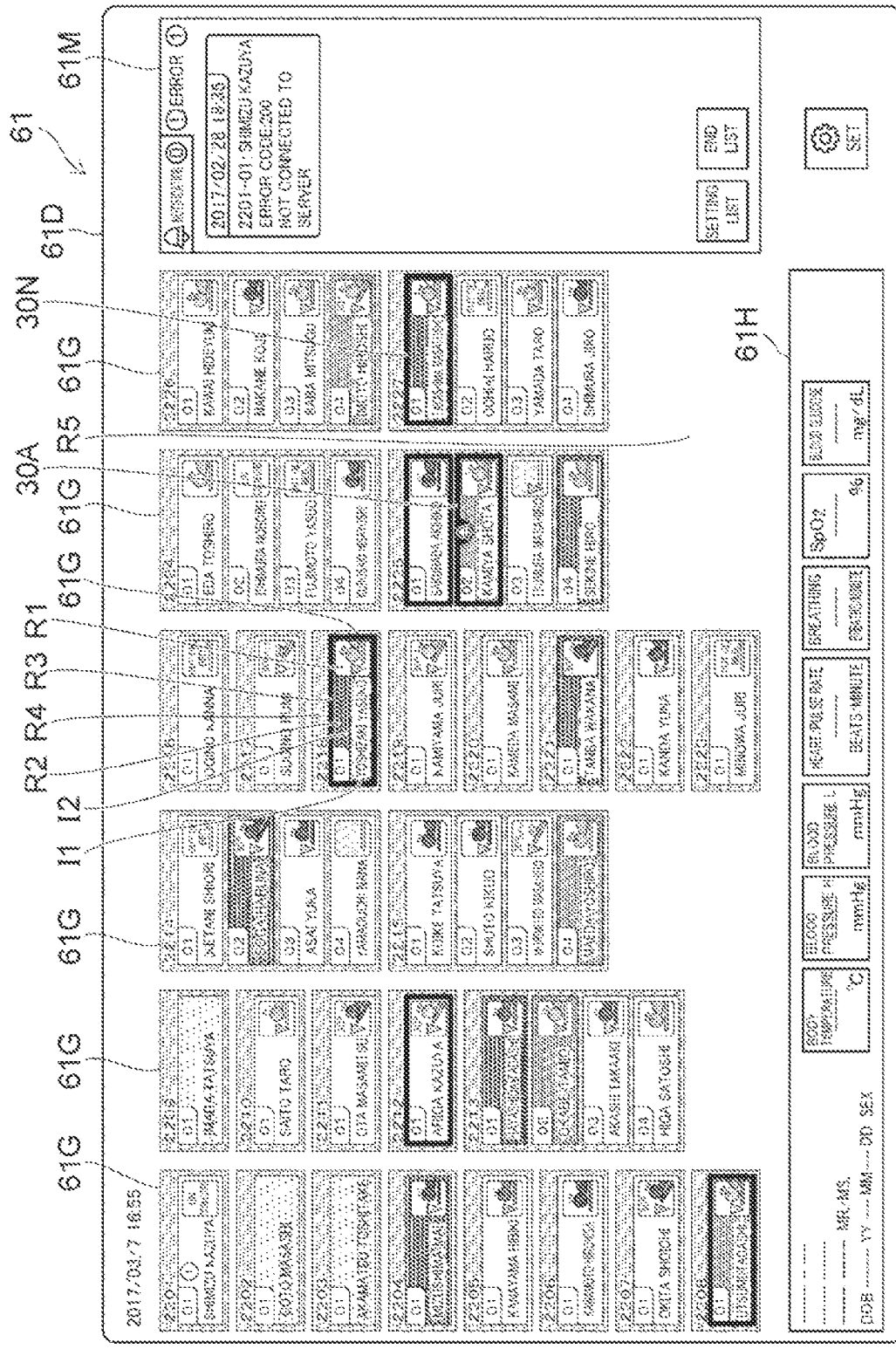
FIG. 2 is a pattern diagram showing an example of a bed system according to an embodiment.

FIG. 2 is a pattern diagram showing an example of a bed system according to an embodiment.

FIG. 2 shows an example of the screen 61D of the first display 61. As shown in FIG. 2, the single screen 61D displays the plurality of images 61G side by side. In this example, a message is displayed in a message region 61M. For example, the message is a communication state error or the like, for example.

One of the plurality of images 61G includes a first partial region R1, a second partial region R2, and a third partial region R3. In this example, an outer edge partial region R4 is further provided. The outer edge partial region R4 is provided on the periphery of the first partial region R1, the second partial region R2, and the third partial region R3. The plurality of images 61G are displayed within a background region R5 of the single screen 61D. The outer edge partial region R4 clarifies a boundary between the background region R5 and the image 61G.

For example, the background region R5 is white, for example. The outer edge partial region R4 is a pale color (pale blue or the like), for example.

At least a part of the second partial region R2 is positioned between the first partial region R1 and the third partial region R3. For example, the third partial region R3 is positioned around the first partial region R1 and the second partial region R2. The third partial region R3 is frame-shaped, for example.

One of the plurality of images 61G corresponds to one of the plurality of user interface devices 55 (a subject user interface device 55). In other words, one of the plurality of images 61G corresponds to one set of the plurality of user interface device information 55i. The subject user interface device 55 corresponds to one bed 51 (the subject bed 51) and one user (the subject user). Accordingly, one of the plurality of images 61G corresponds to the subject bed 51 and the subject user. One of the plurality of images 61G will be described below.

The first display 61 displays a pictogram in the first partial region R1, for example. The first display 61 displays the identification information I1 specifying the user in at least a part of the second partial region R2. The first display 61 displays a warning display 30A in the third partial region R3. Examples of these displays will be described below.

A pictogram is displayed in the first partial region R1. The pictogram includes a state display corresponding to the state information (at least one of the bed state information and the user state information). The pictogram includes the bed moving part information 51i, for example. As described above, the bed moving part information 51i includes information relating to at least one of the height and the angle of one of the plurality of beds 51. For example, the pictogram includes a pattern (including characters) corresponding to the height of the subject bed 51. For example, the pictogram includes a pattern (including characters) corresponding to the angle of the subject bed 51. The pictogram includes the user state information (for example, the vital signs informa-tion and the user behavior information). The pictogram forms at least a part of the state information.

The identification information I1 is displayed in the second partial region R2. In this example, vital signs information I2 is also displayed in the second partial region R2. The identification information I1 specifies the user (the subject user) of one bed (the subject bed 51) among the plurality of beds 51. The identification information I1 includes the name of the subject user, for example. The vital signs information I2 includes information relating to the vital signs of the subject user. The vital signs information I2 includes information relating to at least one of the blood pressure, the blood oxygen saturation, the blood glucose level, the heart rate, the pulse rate, the respiration rate, the weight, and the body temperature of the subject user.

For example, the identification information I1 includes character information (the characters of the name and so on). The vital signs information I2 is displayed according to color. More specifically, in the second partial region R2, the color of the region, excluding the identification information I1, is modified on the basis of the vital signs of the subject user. Thus, the vital signs information I2 may be displayed according to the color on the periphery of the identification information I1. As a result, the condition (the vital signs) of the subject user can be recognized more easily while ensuring that the identification information I1 remains easy to see. An example of display of the vital signs information I2 according to color will be described below.

Hence, the first display 61 displays the identification information I1 and the vital signs information I2 in the second partial region R2. The vital signs information I2 forms at least a part of the state information.

Meanwhile, a warning display 30A is displayed in the third partial region R3. The warning display 30A is displayed when a specific condition is satisfied. When the state information is abnormal, the warning display 30A is displayed in the third partial region R3 of one of the plurality of images 61G. For example, the first display 61 displays the warning display 30A when at least one of the bed-departure state of the subject user, the waking-up state of the subject user, the sitting-up state of the subject user, the sitting-on-the-edge-of-the-bed state of the subject user, the heart rate of the subject user, and the respiration rate of the subject user is abnormal. The first display 61 may also display the warning display 30A in the third partial region R3 when the bed state information is abnormal. As described above, the subject items of the warning display 30A include bed departure, waking up, sitting up, sitting on the edge of the bed, heart rate, respiration rate, and so on. These subject items may be acquired automatically rather than manually, for example. These subject items are acquired continuously without human intervention, for example. Therefore, when an abnormal state occurs among the subject items, it may be difficult to notice the abnormal state. By displaying the warning display 30A in relation to these subject items, more appropriate services can be provided.

A reference (a threshold) for determining whether or not an abnormal state has occurred may be determined in accordance with the state (the condition and so on) of the subject user, for example. For example, when the bed 51 or the auxiliary device 52 of a user who finds walking difficult detects that the user is out of bed, a serious accident such as the user falling from the bed 51 may occur. In this case, a rapid response is necessary. In such cases, the warning display 30A is displayed after detecting the bed departure state. In contrast, when bed departure is detected in relation to a user who finds walking easy, the possibility of a serious accident is comparatively low. In such cases, the warning display 30A need not be displayed even after detecting the bed departure state.

The reference for determining whether or not an abnormal state has occurred may be determined on the basis of a combination of the state of the subject user and the state of the bed 51 or the like, for example. When the bed departure state is detected in relation to a user who finds walking difficult and whose bed 51 is high, the user may fall from the high bed 51. In such cases, the warning display 30A is displayed.

The auxiliary device 52 (or the bed 51) or the like detects information relating to heart rate and respiration rate continuously, for example. As a result, information relating to the steady heart rate and respiration rate of the subject user accumulates. When a dramatic variation from the steady heart rate and respiration rate is observed, the warning display 30A is displayed. When the degree of variation is intermediate, a notification display 30N to be described below may be displayed.

In this example, the notification display 30N is displayed in the third partial region R3. For example, the first display 61 may also display the notification display 30N when at least one of the heart rate of the subject user and the respiration rate of the subject user varies so as to exceed a reference.

For example, the heart rate of the subject user and the respiration rate of the subject user are acquired from the subject bed 51 (one of the plurality of beds) or the auxiliary device 52 of the subject bed 51 (one of the plurality of beds). As described above, the auxiliary device 52 may be considered as a part of the bed 51.

The heart rate of the subject user and the respiration rate of the subject user are detected continuously. When the continuously detected heart rate or respiration rate varies so as to exceed a reference (when an event occurs), the condition of the user may have deteriorated. By displaying the notification display 30N when such evidence of deterioration is found, appropriate countermeasures can be taken rapidly.

The reference used to determine whether or not to display the notification display 30N is determined in accordance with the state of the subject user, for example. A looser reference than the reference used to determine whether or not the display the warning display 30A, for example, is employed as the reference (the threshold) for determining whether or not to display the notification display 30N. For example, a nurse or the like prioritizes care of a user for whom the warning display 30A is displayed over care of a user for whom the notification display 30N is displayed.

By displaying the warning display 30A, the nurse or the like can easily identify the user (the care-receiver) having the highest priority. Further, by displaying the notification display 30N, the nurse or the like can easily identify the user (the care-receiver) having the second highest priority. As a result, the quality of medical or nursing care can be improved, for example.

In this example, a window region 61H is provided on the single screen 61D. At least a part of the information relating to one of the plurality of users, for example, is displayed in the window region 61H. In this example, information relating to the body temperature, the blood pressure (the systolic blood pressure and the diastolic blood pressure), the heart rate, the pulse rate, the respiration rate, the $SpO_2$, and the blood glucose is displayed. By clicking (touching) one of the plurality of images 61G, for example, the information relating to the subject user corresponding to that image 61G is displayed in the window region 61H.

Hence, when one of the plurality of images 61G receives input, the first display 61 may display the information corresponding to that image 61G. This information forms at least a part of the information relating to the subject user corresponding to the image 61G, for example. The information corresponding to this one image among the plurality of images 61G may be displayed in a part of the single screen 61D, for example (in the window region 61H, for example). By providing the window region 61H on the same screen 61D, the warning display 30A can be presented to a nurse or the like even while the caregiver or the like is viewing the information displayed in the window region 61H, for example. As a result, cases in which the warning display 30A and so on are overlooked can be suppressed.

In an embodiment, the window region 61H may be provided on a separate screen. For example, when one of the plurality of images 61G receives input, the single screen 61D may shift to a different screen. In this case, a different screen can be used, and therefore information relating to the subject user can be displayed in detail.

Several examples of the images 61G will be described below.

FIGS. 3(a) to 3(d) are pattern diagrams showing examples of images displayed in a bed system according to an embodiment.

Figure 3A:
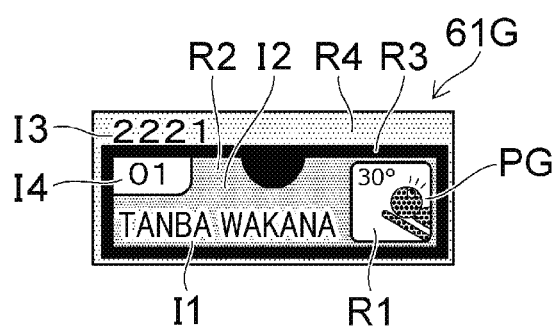
FIGS. 3(a) to 3(d) are pattern diagrams showing examples of images displayed in a bed system according to an embodiment.

As shown in FIG. 3(a), the single image 61G is provided with the first partial region R1, the second partial region R2, and the third partial region R3. In this example, an outer edge partial region R4 is further provided. The ward number I3 (in this example, "2221") of the subject user may be displayed in the outer edge partial region R4.

As described above, the pictogram PG is displayed in the first partial region R1. The identification information I1 and the vital signs information I2 are displayed in the second partial region R2. In this example, the number 14 (in this example, "01") of the subject user within the ward is displayed in a part of the second partial region R2.

Figure 3B:
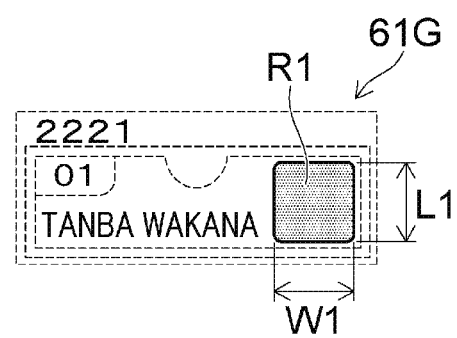
Figure 3C:
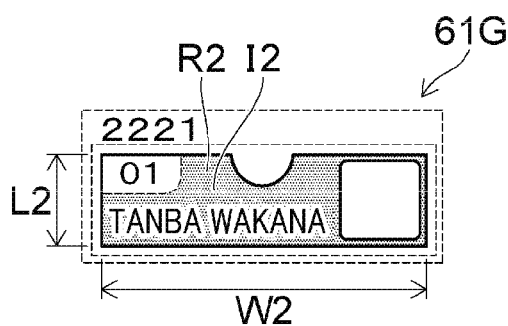
Figure 3D:
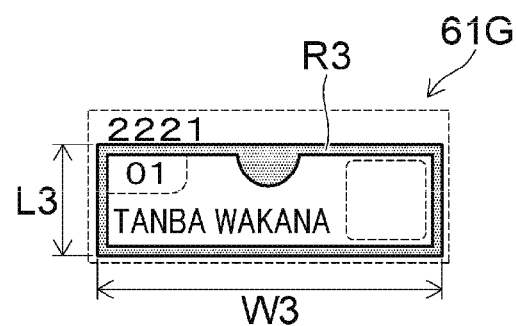

FIG. 3(b) shows an example of the first partial region R1. FIG. 3(c) shows an example of the second partial region R2. FIG. 3(d) shows an example of the third partial region R3.

As shown in FIG. 3(b), the first partial region R1 has a vertical direction length L1 and a lateral direction length W1. As shown in FIG. 3(c), the second partial region R2 has a vertical direction length L2 and a lateral direction length W2. As shown in FIG. 3(d), the third partial region R3 has a vertical direction length L3 and a lateral direction length W3.

In an embodiment, the length L3 is greater than the length L1. The length L3 is greater than the length L2. The length W3 is greater than the length W1. The length W3 is greater than the length W2.

Hence, the vertical direction length L3 and the lateral direction length W3 of the third partial region R3 are long. Accordingly, the outer shape of the third partial region R3 is larger than the outer shape of the first partial region R1 and the outer shape of the second partial region R2. Thus, for example, the warning display 30A or a notification display 30N displayed in the third partial region R3 is clearly visible.

A nurse or the like can identify necessary warnings and notifications in an easily understandable manner.

Meanwhile, for example, the surface area of the second partial region R2 is greater than the surface area of the first partial region R1. For example, the surface area of the vital signs information I2 displayed in the second partial region R2 is greater than the surface area of the pictogram PG displayed in the first partial region R1. The vital signs information I2 often has a higher priority than the information acquired from the pictogram PG. With this surface area relationship, a nurse or the like can identify high-priority information (the vital signs information I2) preferentially.

Examples of displays displayed in the third partial region R3 will be described below.

Figure 4A:
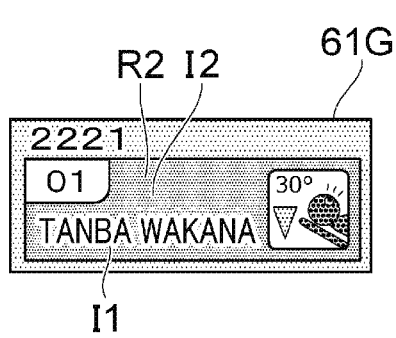
FIGS. 4(a) to 4(c) are pattern diagrams showing examples of images displayed in a bed system according to an embodiment.
Figure 4B:
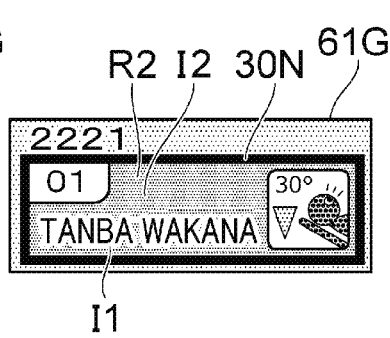
Figure 4C:
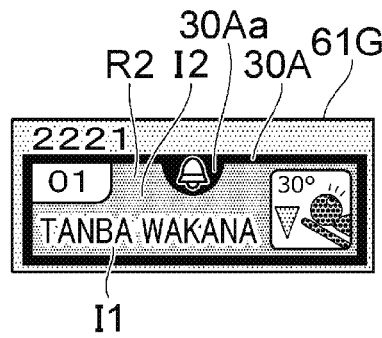

FIGS. 4(a) to 4(c) are pattern diagrams showing examples of images displayed in a bed system according to an embodiment.

FIG. 4(a) shows a state in which no information is displayed in the third partial region R3. FIG. 4(b) shows a state in which the notification display 30N is displayed in the third partial region R3. FIG. 4(c) shows a state in which the warning display 30A is displayed in the third partial region R3.

As shown in FIG. 4(a), when no information is displayed in the third partial region R3, the state of the third partial region R3 is identical to the state of at least a part of the second partial region R2. For example, the color of the third partial region R3 is the same as the color of the vital signs information I2 in the second partial region R2.

The recognizability of the notification display 30N shown in FIG. 4(b) is higher than the recognizability of the vital signs information I2 in the second partial region R2, for example. The color of the notification display 30N is dark red, for example. The vital signs information I2, on the other hand, is displayed in a pale color (pale pink, pale yellow, pale green, pale blue, or the like, for example). The notification display 30N can thus be recognized more easily.

An attention-alerting property (the recognizability) of the warning display 30A shown in FIG. 4(c) is higher than the attention-alerting property (the recognizability) of the notification display 30N, for example. For example, the warning display 30A may include flashing. The notification display 30N, on the other hand, does not flash. The warning display 30A includes a distinctively shaped pattern 30Aa, for example. The distinctively shaped pattern 30Aa is not provided in the notification display 30N. In this example, the distinctively shaped pattern 30Aa is displayed in the shape of a "bell". Due to the distinctively shaped pattern 30Aa, the surface area of the warning display 30A is larger than the surface area of the notification display 30N. Thus, the warning display 30A has at least one of a larger surface area than the notification display 30N and a different pattern to the pattern included in the notification display 30N, for example. As a result, the attention-alerting property of the warning display 30A is higher than the attention-alerting property of the notification display 30N.

The color of the warning display 30A may be different to the color of the notification display 30N. For example, the warning display 30A is dark red. The notification display 30N may have a red color that is paler than the color of the warning display 30A. For example, the chroma of the warning display 30A may be higher than the chroma of the notification display 30N.

As shown in FIG. 4(c), the region displaying the distinctively shaped pattern 30Aa forming a part of the warning display 30A is considered part of the third partial region R3. As shown in FIGS. 4(a) and 4(b), when the warning display 30A is not displayed, this part of the third partial region R3 is identical to the state of at least a part of the second partial region R2. For example, the color of this part of the third partial region R3 is the same as the color of the vital signs information I2 in the second partial region R2.

Examples of displays displayed in the second partial region R2 will be described below.

Figures 5A, 5B, 5C:
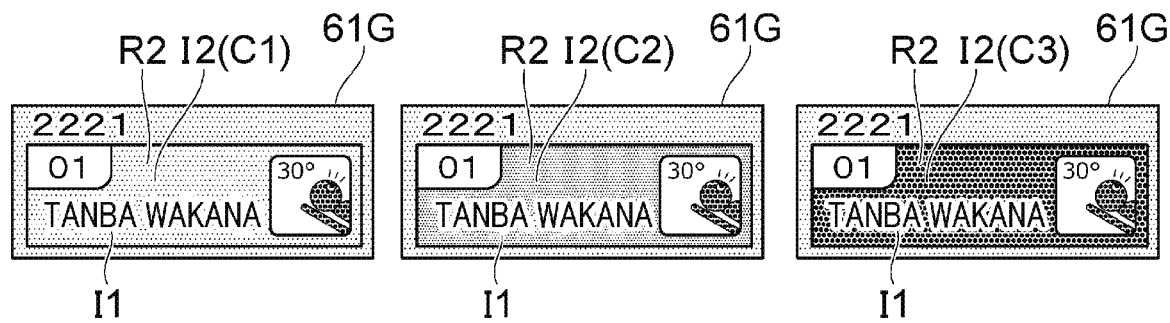
FIGS. 5(a) to 5(c) are pattern diagrams showing examples of images displayed in a bed system according to an embodiment.

FIGS. 5(a) to 5(c) are pattern diagrams showing examples of images displayed in a bed system according to an embodiment.

These figures correspond to the plurality of information displayed in the second partial region R2. As described above, the identification information I1 (character information such as a name, for example) and the vital signs information I2 (color information, for example) are displayed in the second partial region R2. For example, at least a part of the vital signs information I2 is between the identification information I1 and the third partial region R3 (the warning display 30A and the notification display 30N).

In this example, the vital signs information I2 is displayed according to color. In this example, the vital signs information I2 is displayed using three colors (a first color C1, a second color C2, and a third color C3). FIGS. 5(a) to 5(c) correspond respectively to the three colors.

The first color C1, shown in FIG. 5(a), corresponds to "normal", for example. The second color C2, shown in FIG. 5(b), corresponds to "caution". The third color C3, shown in FIG. 5(c), corresponds to "warning".

For example, the chroma of the third color C3 is higher than the chroma of the second color C2. The chroma of the second color C2 is higher than the chroma of the first color C1. The third color C3 is darker than the second color C2. The second color C2 is darker than the first color C1. As a result, for example, the third color C3 is more easily recognizable than the other two colors. As a result, the second color C2 is more easily recognizable than the first color C1.

For example, the third color C3 is a color close to red. The first color C1 is a color distant from red. For example, an absolute value of a difference between a hue of the third color C3 and a hue of red is smaller than an absolute value of a difference between a hue of the second color C2 and the hue of red. For example, the absolute value of the difference between the hue of the second color C2 and the hue of red is smaller than an absolute value of a difference between a hue of the first color C1 and the hue of red.

For example, the third color C3 is pale red. The second color C2 is pale yellow. The first color C1 is substantially white.

When the warning display 30A (or the notification display 30N) displayed in the third partial region R3 is a red-based color, the color of the warning display 30A (or the notification display 30N) is darker than the color (pale red, for example) of the third color C3.

For example, the chroma of the notification display 30N is higher than the chroma of the display of the vital signs information I2. The chroma of the notification display 30N is higher than the chroma of the first color C1, higher than the chroma of the second color C2, and higher than the chroma of the third color C3. As a result, the attention-drawing ability of the notification display 30N can be enhanced.

For example, an absolute value of a difference between a hue of the notification display 30N and the hue of red is smaller than an absolute value of a difference between a hue of the display of the vital signs information I2 and the hue of red. For example, the absolute value of the difference between the hue of the notification display 30N and the hue of red is smaller than the absolute value of the difference between the hue of the first color C1 and the hue of red. The absolute value of the difference between the hue of the notification display 30N and the hue of red is smaller than the absolute value of the difference between the hue of the second color C2 and the hue of red. The absolute value of the difference between the hue of the notification display 30N and the hue of red is smaller than the absolute value of the difference between the hue of the third color C3 and the hue of red. As a result, the attention-drawing ability of the notification display 30N can be enhanced.

For example, the chroma of the warning display 30A is higher than the chroma of the display of the vital signs information I2. For example, the chroma of the warning display 30A is higher than the chroma of the first color C1, higher than the chroma of the second color C2, and higher than the chroma of the third color C3. As a result, the attention-drawing ability of the warning display 30A can be enhanced.

For example, an absolute value of a difference between a hue of the warning display 30A and the hue of red is smaller than the absolute value of the difference between the hue of the display of the vital signs information I2 and the hue of red. For example, the absolute value of the difference between the hue of the warning display 30A and the hue of red is smaller than the absolute value of the difference between the hue of the first color C1 and the hue of red. The absolute value of the difference between the hue of the warning display 30A and the hue of red is smaller than the absolute value of the difference between the hue of the second color C2 and the hue of red. The absolute value of the difference between the hue of the warning display 30A and the hue of red is smaller than the absolute value of the difference between the hue of the third color C3 and the hue of red. As a result, the attention-drawing ability of the warning display 30A can be enhanced.

For example, the vital signs information I2 has a pale color. The vital signs information I2 is displayed close to the identification information I1. When the vital signs information I2 has a dark color, the recognizability of the identification information I1 deteriorates. By displaying the vital signs information I2 in a pale color, a nurse or the like can identify the desired vital signs information I2 in an easily understandable manner while the identification information I1 remain highly recognizable.

For example, when the warning display 30A or the notification display 30N is displayed, the identification information I1 is preferably clearly visible. Thus, the caregiver or the like can identify the user in relation to whom a warning or a notification has been issued in an easily understandable manner. The identification information I1 is preferably black (a dark color), for example. Thus, high recognizability is acquired in relation to the identification information I1.

The display of the vital signs information I2, meanwhile, is displayed according to color. As a result, the caregiver or the like can recognize the medical condition of the subject user intuitively, in an easily understandable manner. The color is comparatively pale. Thus, deterioration of the recognizability of the identification information I1 can be suppressed.

The warning display 30A (or the notification display 30N) needs to have a superior attention-drawing ability. By making the color of the display of the vital signs information I2 comparatively pale, the attention-drawing ability of the warning display 30A (or the notification display 30N) can be enhanced.

As described above, at least a part of the pale-colored vital signs information I2 is between the identification information I1 and the third partial region R3 (the warning display 30A and the notification display 30N). Thus, a situation in which the identification information I1 becomes difficult to see when the warning display 30A or the notification display 30N is displayed can be suppressed.

As described above, the third partial region R3 in which the warning display 30A or the notification display 30N is displayed has a larger outer shape than the first partial region R1 and the second partial region R2. As a result, a superior attention-drawing ability is acquired in relation to the warning display 30A or the notification display 30N. By making the color of the vital signs information I2 pale, the identification information I1 remains clearly visible even when the warning display 30A or the notification display 30N is displayed.

By combining the second partial region R2 and the third partial region R3 in this manner, the warning display 30A or the notification display 30N can be recognized in an easily understandable manner. Further, since the vital signs information I2 is displayed in the second partial region R2 according to color, the caregiver or the like can recognize the medical condition of the subject user intuitively, in an easily understandable manner.

In an embodiment, as described above, the pictogram PG is displayed in the first partial region R1. Hence, from the single image 61G, the caregiver or the like can easily recognize the overall situation, including the state of the subject bed 51 (the bed moving part information 51i) and the state of the subject user (the user behavior information 52i) in an easily understandable manner.

The real-time property of the warning display 30A or the notification display 30N is superior to that of the vital signs information I2. A bold color is used for the warning display 30A or the notification display 30N having a superior real-time property. As a result, the warning display 30A or the notification display 30N can be recognized rapidly.

Several examples of the pictogram PG displayed in the first partial region R1 will be described below.

Figure 6A:
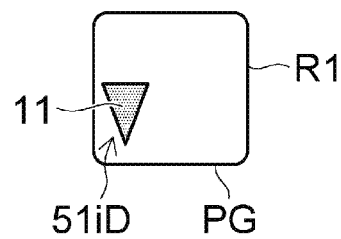
FIGS. 6(a) and 6(b) are pattern diagrams showing examples of images displayed in a bed system according to an embodiment.
Figure 6B:
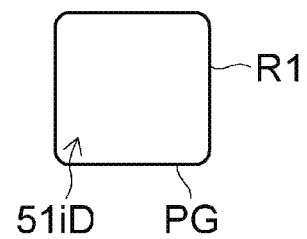

FIGS. 6(a) and 6(b) are pattern diagrams showing examples of images displayed in a bed system according to an embodiment.

These figures show examples of the pictogram PG. In these examples, the information (the bed moving part information 51i) relating to the subject bed 51 is displayed by a bed moving part display 51iD.

As shown in FIG. 6(a), in this example, the height of the subject bed 51 is displayed using a height display pattern 11. In this example, the height display pattern 11 has a downward-pointing triangular shape. When the height display pattern 11 is displayed, the height of the bed is low (at the lowest level, for example).

As shown in FIG. 6(b), the height display pattern 11 is not displayed, for example. This state indicates that the height of the bed is high (above floor level, for example), for example.

Thus, the presence or absence of a display pattern (the height display pattern 11 or the like) can be used as the bed moving part display 51iD.

FIGS. 7(a) to 7(j) are pattern diagrams showing examples of images displayed in a bed system according to an embodiment.

These figures show examples of the pictogram PG. In these examples, an angle display pattern 12 and angle display characters 13 are used as the bed moving part display 51iD of the pictogram PG.

Figure 7A:
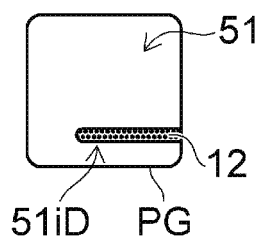
FIGS. 7(a) to 7(j) are pattern diagrams showing examples of images displayed in a bed system according to an embodiment.
Figure 7B:
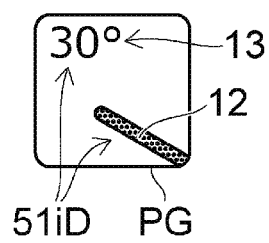
Figure 7C:
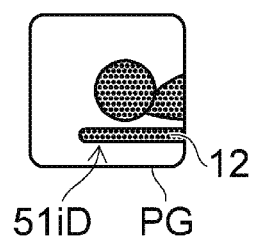
Figure 7D:
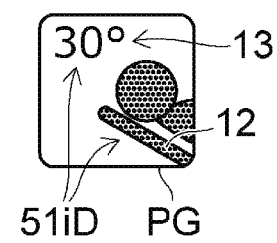
Figure 7E:
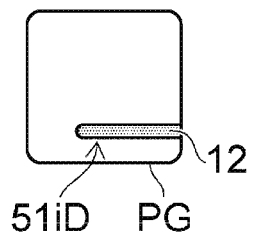
Figure 7F:
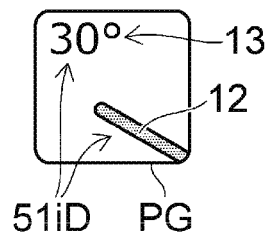
Figure 7G:
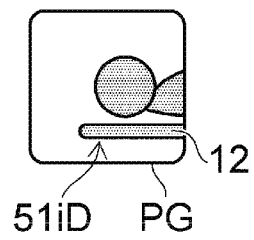
Figure 7H:
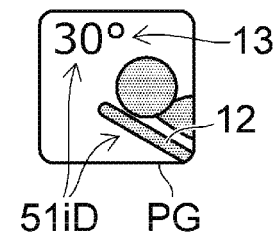
Figure 7I:
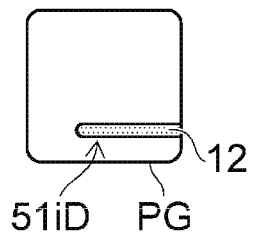

In the examples shown in FIGS. 7(a), 7(c), 7(e), 7(g), and 7(i), the angle display pattern 12 extends in a lateral direction (a horizontal direction). This angle display pattern 12 indicates that the angle of the bed 51 (the angle of the back section 70a, for example) is small (a horizontal state in which the angle is 0 degrees, for example). FIGS. 7(a), 7(e), and 7(i) are used when the subject user is out of the bed 51 (i.e. in a bed departure state), for example. FIGS. 7(c) and 7(g) are used when the subject user is lying flat on the bed 51, for example.

Figure 7J:
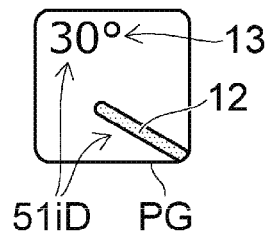
Figure 8A:
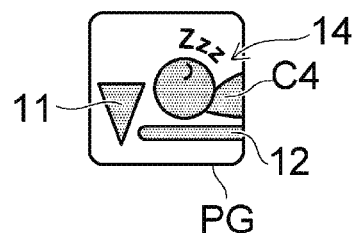
FIGS. 8(a) to 8(l) are pattern diagrams showing examples of images displayed in a bed system according to an embodiment.
Figure 8B:
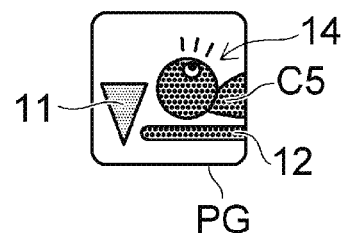
Figure 8C:
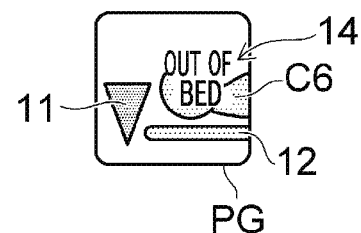
Figure 8D:
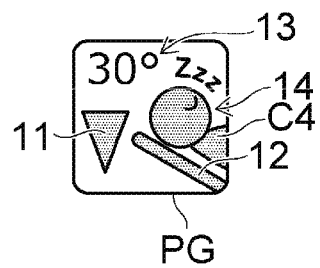
Figure 8E:
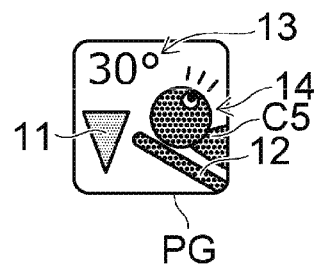
Figure 8F:
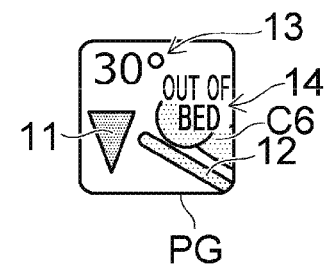
Figure 8G:
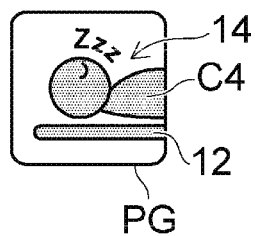
Figure 8H:
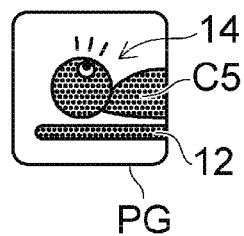
Figure 8I:
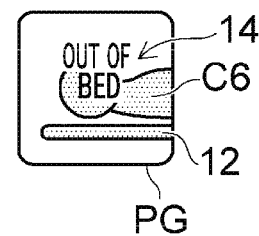
Figure 8J:
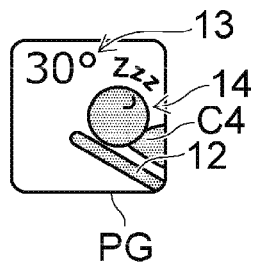
Figure 8K:
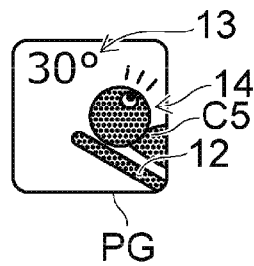
Figure 8L:
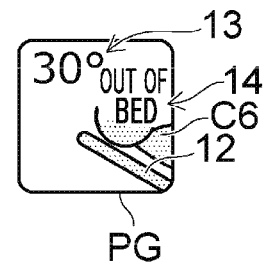
Figures 9A, 9B, 9C, 9D:
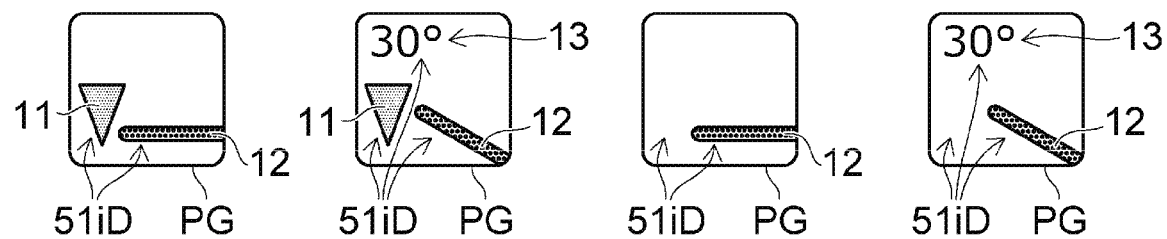
FIGS. 9(a) to 9(d) are pattern diagrams showing examples of images displayed in a bed system according to an embodiment.

In the examples shown in FIGS. 7(b), 7(d), 7(f), 7(h), and 7(j), the angle display pattern 12 is inclined. This angle display pattern 12 indicates that the angle of the bed 51 is large (30 degrees or the like, for example). In these examples, the angle display characters 13 indicating the approximate angle of incline are also displayed. FIGS. 7(b), 7(f), and 7(j) are used when the subject user is out of the bed 51 (i.e. in a bed departure state), for example. FIGS. 7(d) and 7(h) are used when the subject user is lying flat on the bed 51, for example. It is acceptable to display at least one of the angle display pattern 12 and the angle display characters 13.

The color of the angle display pattern 12 in FIGS. 7(a) to 7(d) is different to the color of the angle display pattern 12 in FIGS. 7(e) to 7(h). The color of the angle display pattern 12 in FIGS. 7(a) to 7(d) is different to the color of the angle display pattern 12 in FIGS. 7(i) and 7(j). The color of the angle display pattern 12 in FIGS. 7(e) to 7(h) is different to the color of the angle display pattern 12 in FIGS. 7(i) and 7(j). As will be described below, these colors may be determined in accordance with the state of the subject user, such as waking up, sleeping, and bed departure, for example.

FIGS. 8(a) to 8(l) are pattern diagrams showing examples of images displayed in a bed system according to an embodiment.

These figures show examples of the pictogram PG. In these examples, the height display pattern 11, the angle display pattern 12, the angle display characters 13, and a user behavior display 14 are displayed as the pictogram PG. The user behavior display 14 corresponds to the user behavior information 52i. As described above, the user behavior information 52i includes information relating to the user behavior state, including at least one of bed departure, sleeping, waking up, sitting up, and sitting on the edge of the bed, in relation to the user of the bed 51. In this example, the user behavior state is classified as one of three states, namely sleeping, waking up, and bed departure. Three display patterns are used as the user behavior display 14.

In the examples shown in FIGS. 8(a), 8(d), 8(g), and 8(j), the user behavior display 14 corresponding to sleeping is displayed. In the examples shown in FIGS. 8(b), 8(e), 8(h), and 8(k), the user behavior display 14 corresponding to waking up is displayed. In the examples shown in FIGS. 8(c), 8(f), 8(i), and 8(l), the user behavior display 14 corresponding to bed departure is displayed.

As illustrated by these figures, the single pictogram PG includes a set of the height display pattern 11, the angle display pattern 12, the angle display characters 13, and the user behavior display 14.

The color (a fourth color C4) of the user behavior display 14 corresponding to sleeping may differ from the color (a fifth color C5) of the user behavior display 14 corresponding to waking up. The fourth color may differ from the color (a sixth color C6) of the user behavior display 14 corresponding to bed departure. The fifth color C5 may differ from the sixth color C6.

For example, when the user is awake on the bed 51, the possibility of an accident or the like may be higher than when the user is asleep on the bed 51. Therefore, the attention-drawing ability of the color (the fifth color C5) used when the user is awake on the bed 51 is preferably higher than the attention-drawing ability of the color (the fourth color C4) used when the user is asleep on the bed 51.

For example, the chroma of the fifth color C5 is higher than the chroma of the fourth color C4. For example, the absolute value of the difference between the hue of the fifth color C5 and the hue of red is smaller than the absolute value of the difference between the hue of the fourth color C4 and the hue of red. For example, the fourth color C4 is pale blue and the fifth color C5 is pale yellow.

When the user is out of bed, meanwhile, it is impossible to ascertain another state of the user from the information acquired from the bed 51 (or the auxiliary device 52). Hence, the color (the sixth color C6) used when the user is out of bed may be an unobtrusive color. For example, the chroma of the sixth color C6 is lower than the chroma of the fourth color C4. For example, the sixth color C6 is gray.

FIGS. 9(a) to 9(d) are pattern diagrams showing examples of images displayed in a bed system according to an embodiment.

These figures correspond to cases in which the pictogram PG displays the bed moving part display 51iD (information relating to the subject bed 51) but does not display the user behavior display 14 (sleeping, waking up, bed departure, and so on, for example). The height display pattern 11, the angle display pattern 12, and the angle display characters 13 are displayed as the bed moving part display 51iD of the pictogram PG.

Figure 10A:
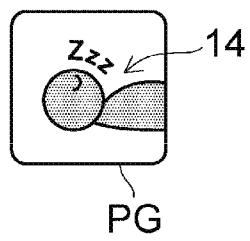
FIGS. 10(a) to 10(c) are pattern diagrams showing examples of images displayed in a bed system according to an embodiment.
Figure 10B:
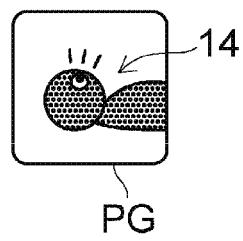
Figure 10C:
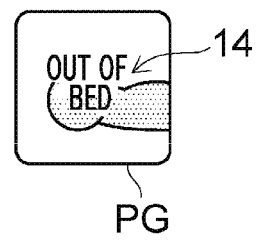

FIGS. 10(a) to 10(c) are pattern diagrams showing examples of images displayed in a bed system according to an embodiment.

These figures correspond to cases in which the pictogram PG does not display the bed moving part display 51iD but does display the user behavior display 14 (sleeping, waking up, bed departure, and so on, for example).

Thus, various modifications can be applied to the pictogram PG.

For example, in an embodiment, information such as the state of the bed 51, the behavior state of the user of the bed 51, and the medical condition of the user, for example, is presented in a location (a remote location) away from the bed 51. The state of the bed 51 includes an operation state, a setting state, an error state, and so on of the bed 51. The state of the bed 51 may also include the state of the user interface device (an operation state, a setting state, an error state, and so on). The behavior state of the user includes at least one of bed departure, sleeping, waking up (lying flat on the bed), sitting up, and sitting on the edge of the bed, for example. The medical condition of the user includes normal, poor, critical, and so on, for example. The medical condition of the user includes at least one of heart rate, respiration rate, blood pressure, blood oxygen saturation, blood glucose level, and body temperature, for example. On the basis of the state of the bed 51, the behavior state of the user of the bed 51, the medical condition of the user, and so on, a doctor, a nurse, or the like, for example, implements treatment, issues instructions, confirms risk, and so on. By presenting the state of the bed 51, the behavior state of the user, the medical condition of the user, and so on in relation to the plurality of beds 51 on a single screen in a remote location, a nurse or the like can recognize the information quickly and efficiently.

In an embodiment, information having a superior real-time property (the warning display 30A or the notification display 30N) is displayed in a large size (vertical direction length and lateral direction length) and in a bold color, for example. Meanwhile, high-priority information (the vital signs information I2 and so on, for example) is displayed over a large surface area in a pale color or the like. Further, information relating to the state of the bed 51 and the state of the user (the bed moving part information 51*i* and the user behavior information 52*i*, for example) is combined and displayed using the pictogram PG.

Hence, when a plurality of information is displayed on the single screen 61D in relation to the plurality of beds 51, an improvement in the recognizability (including the attention-drawing ability) of the plurality of information can be expected.

The user interface device 55 is provided for each of the plurality of beds 51. As a result, information relating to the plurality of beds 51 and the plurality of users can be collected from each bed 51. The information acquired by the plurality of user interface devices 55 is supplied to the acquisition unit 61I via a server, for example.

According to an embodiment, a nurse or the like, for example, can collect information more quickly. Risks can be ascertained early, leading to an improvement in the quality of medical care or nursing care.

The bed system 110 according to an embodiment may further include the plurality of beds 51. The plurality of user interface devices 55 are connected respectively to the plurality of beds 51. The bed system 110 may further include the auxiliary device 52. The bed system 110 may further include a second display 62. The bed system 110 may further include the server 65. The bed system 110 may further include an electronic medical record storage unit 66.

As described above, one (each) of the plurality of bed devices 50 includes the bed 51 and the user interface device 55. The user interface device 55 is connected to the bed 51. The user interface device 55 may be provided as a separate component to the bed 51, for example. For example, the user interface device 55 may be provided separately to the bed 51 (or components (a side rail, a frame, and so on) included in the bed 51). By providing the user interface device 55 as a separate component to the bed 51, the combination of the bed 51 and the user interface device 55 can be modified, for example. As a result, various situations can be dealt with easily, leading to a further improvement in usability.

An example of the first input/output device 60 will now be described.

Figure 11:
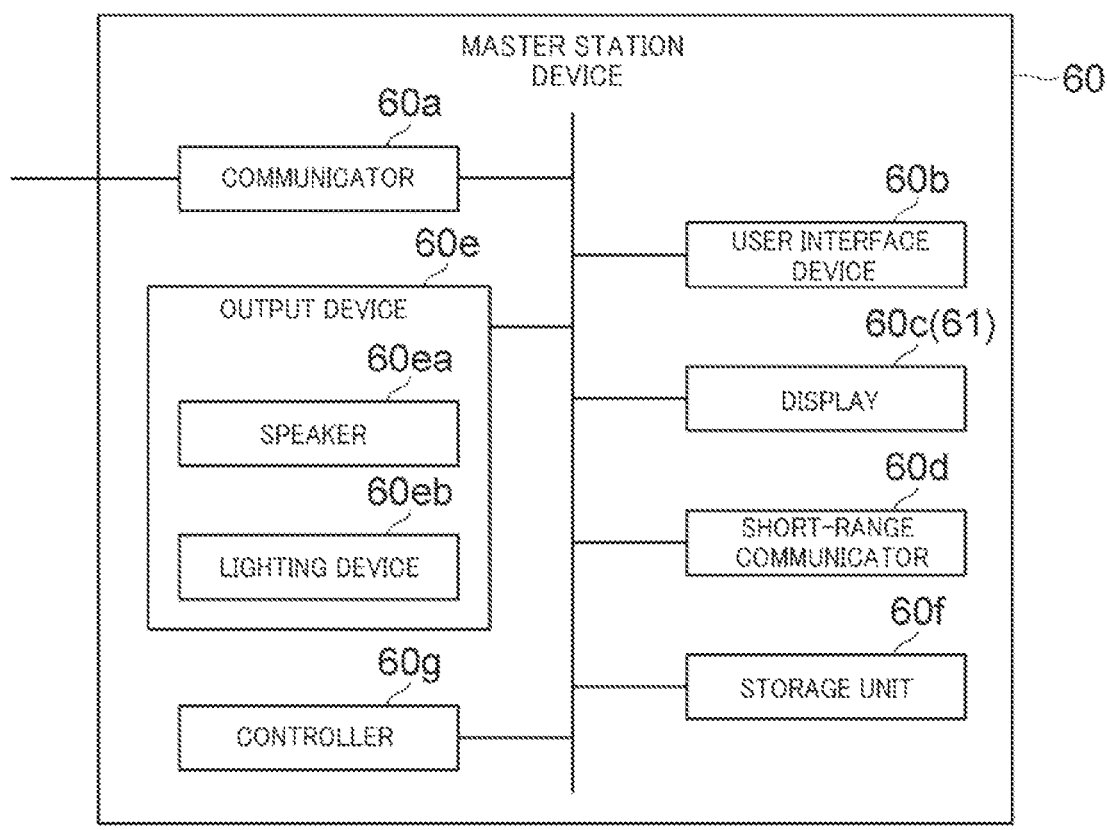
FIG. 11 is a pattern diagram showing an example of a part of a bed system according to an embodiment.

FIG. 11 is a pattern diagram showing an example of a part of a bed system according to an embodiment.

FIG. 11 is a block diagram of the first input/output device 60. As shown in FIG. 11, the first input/output device 60 includes, for example, a communicator 60*a*, a user interface device 60*b* (an input reception unit), a display 60*c* (the first display 61, for example), a short-range communicator 60*d*, an output device 60*e*, a storage unit 60*f*, and a controller 60*g* (a processing unit).

The communicator 60*a* includes a communication interface circuit, for example. The communicator 60*a* communicates with another device (the plurality of bed devices 50, for example) using a wired or wireless method selected as desired. For example, communication may be performed via the server 65.

The user interface device 60*b* includes a keyboard, a pointing device (a mouse, a tablet, or the like), and buttons or a touch panel, for example. The user interface device 60*b* receives input.

The display 60*c* includes a display device. The display 60*c* displays information, for example. The display 60*c* may display at least one of the notification display 30N and the warning display 30A, for example. The display 60*c*, the user interface device 60*b*, and the display 60*c* may be integrated.

The short-range communicator 60*d* communicates with various devices, for example. For example, communication is performed between an identification tag or the like carried by the caregiver or the like and the short-range communicator 60*d*. As a result, the caregiver or the like is identified and so on. Communication by the short-range communicator 60*d* is based on a wireless system, for example.

The output device 60*e* includes at least one of a speaker 60*ea* (a speaker or the like, for example) and a lighting device 60*eb* (a light-emitting element or the like, for example), for example. The output device 60*e* issues reports, for example.

The storage unit 60*f* includes a magnetic hard disk device, a semiconductor storage device, or the like, for example. The storage unit 60*f* stores the plurality of user interface device information 55*i*, for example. The storage unit 60*f* stores a program of the processing executed by the controller 60*g* and so on, for example.

The controller 60*g* includes an electronic circuit (a CPU: Central Processing Unit or the like, for example), for example. The controller 60*g* executes processing based on the program, for example. For example, the controller 60*g* compares the measurement values with the set values and so on, for example. The controller 60*g* then causes at least one of the display 60*c* and the output device 60*e* to issue a report in accordance with the comparison result.

Figure 12:
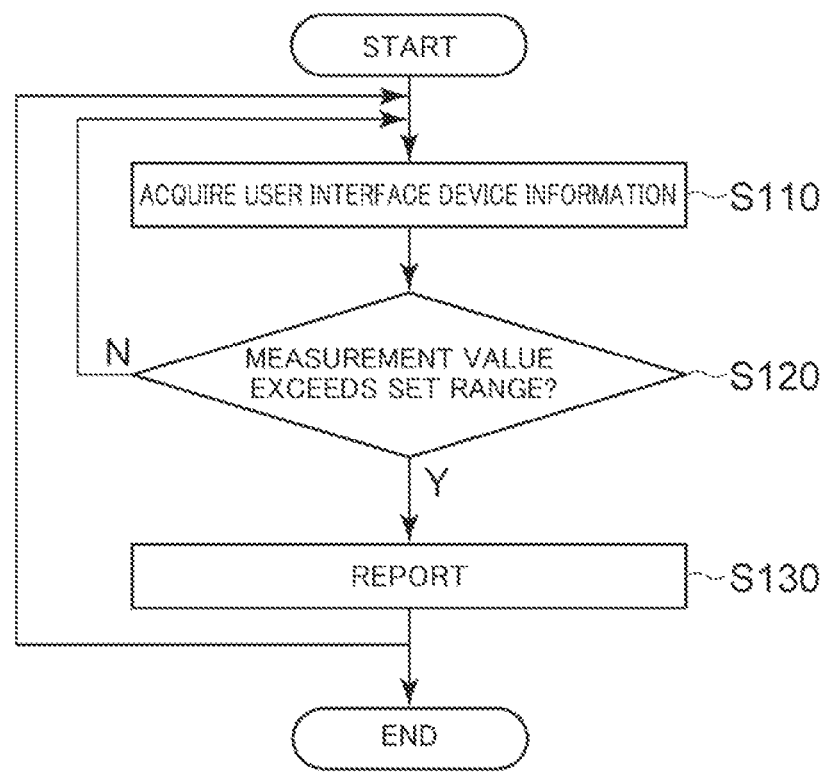
FIG. 12 is a flowchart showing an example of an operation performed in a bed system according to an embodiment.

FIG. 12 is a flowchart showing an example of an operation performed in a bed system according to an embodiment.

FIG. 12 shows an operation performed by a controller (the controller 60*g*, for example) according to an embodiment. For example, the controller 60*g* acquires the user interface device information 55*i* (step S110). The user interface device information 55*i* includes the measurement values of the plurality of items in the plurality of bed devices 50. The controller 60*g* determines whether or not the measurement values exceed set ranges (a range determined by the first set value, a range determined by the first set value, and so on). When a measurement value exceeds a set range, the controller 60*g* causes another device (the display 60*c*, the output device 60*e*, or the like) to issue a report (step S130). The processing then returns to step S110. When the measurement values do not exceed the set ranges, on the other hand, the processing returns to step S110. By implementing this processing, reports are issued appropriately.

Figure 13:
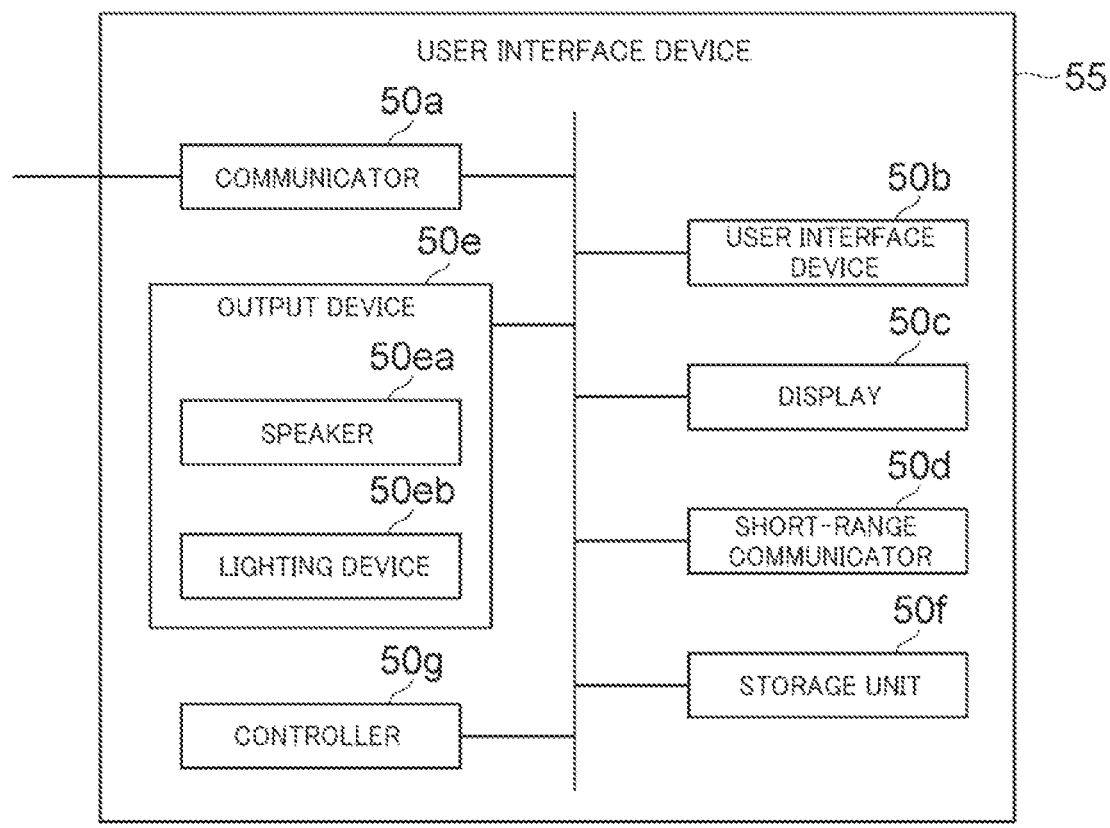
FIG. 13 is a pattern diagram showing an example of a part of a bed system according to an embodiment.

Examples of the user interface device 55, the second display 62, and the server 65 will be described below. FIG. 13 is a pattern diagram showing an example of a part of a bed system according to an embodiment.

FIG. 13 is a block diagram of the user interface device 55. As shown in FIG. 13, the user interface device 55 includes, for example, a communicator 50*a*, a user interface device 50*b* (an input reception unit), a display 50*c*, a short-range communicator 50*d*, an output device 50*e*, a storage unit 50*f*, and a controller 50*g* (a processing unit). The output device 50*e* includes at least one of a speaker 50*ea* (a speaker or the like, for example) and a lighting device 50*eb* (a light-emitting element or the like, for example), for example.

Figure 14:
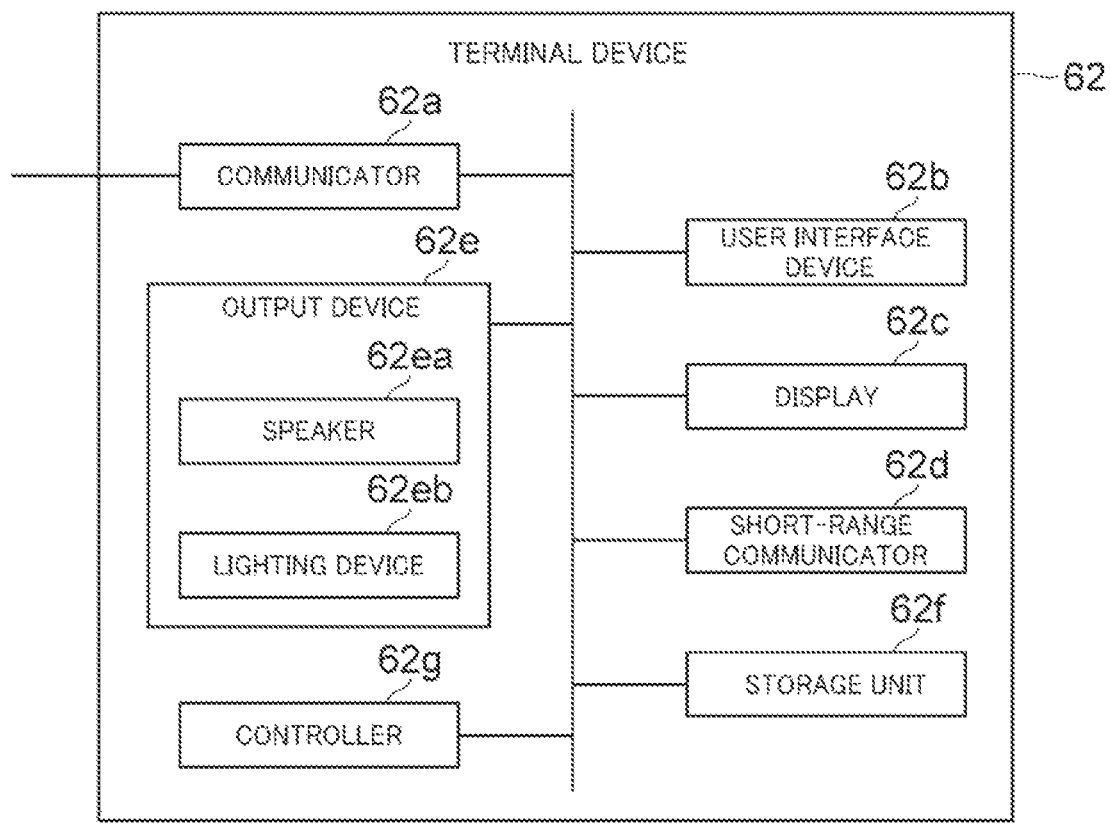
FIG. 14 is a pattern diagram showing an example of a part of a bed system according to an embodiment.

FIG. 14 is a pattern diagram showing an example of a part of a bed system according to an embodiment.

FIG. 14 is a block diagram of a terminal device including the second display 62. As shown in FIG. 14, the terminal device includes, for example, a communicator 62*a*, a user interface device 62*b* (an input reception unit), a display 62*c*, a short-range communicator 62*d*, an output device 62*e*, a storage unit 62*f*, and a controller 62*g* (a processing unit). The output device 62*e* includes at least one of a speaker 62*ea* (a speaker or the like, for example) and a lighting device 62*eb* (a light-emitting element or the like, for example), for example.

The configuration described in relation to the communicator 60a can be applied to the communicator 50a and the communicator 62a. The configuration described in relation to the user interface device 60b can be applied to the user interface device 50b and the user interface device 62b. The configuration described in relation to the display 60c can be applied to the display 50c and the display 62c. The configuration described in relation to the short-range communicator 60d can be applied to the short-range communicator 50d and the short-range communicator 62d. The configuration described in relation to the output device 60e can be applied to the output device 50e and the output device 62e. The configuration described in relation to the storage unit 60f can be applied to the storage unit 50f and the storage unit 62f. The configuration described in relation to the controller 60g can be applied to the controller 50g and the controller 62g. The controller 50g and the controller 62g may implement the operation (see FIG. 12) described in relation to the controller 60g.

The terminal device including the second display 62 may issue the report, for example. At least one of the plurality of user interface devices 55 may issue the report, for example. When one of the plurality of user interface devices 55 issues the report, a report relating to that user interface device 55 is issued.

Figure 15:
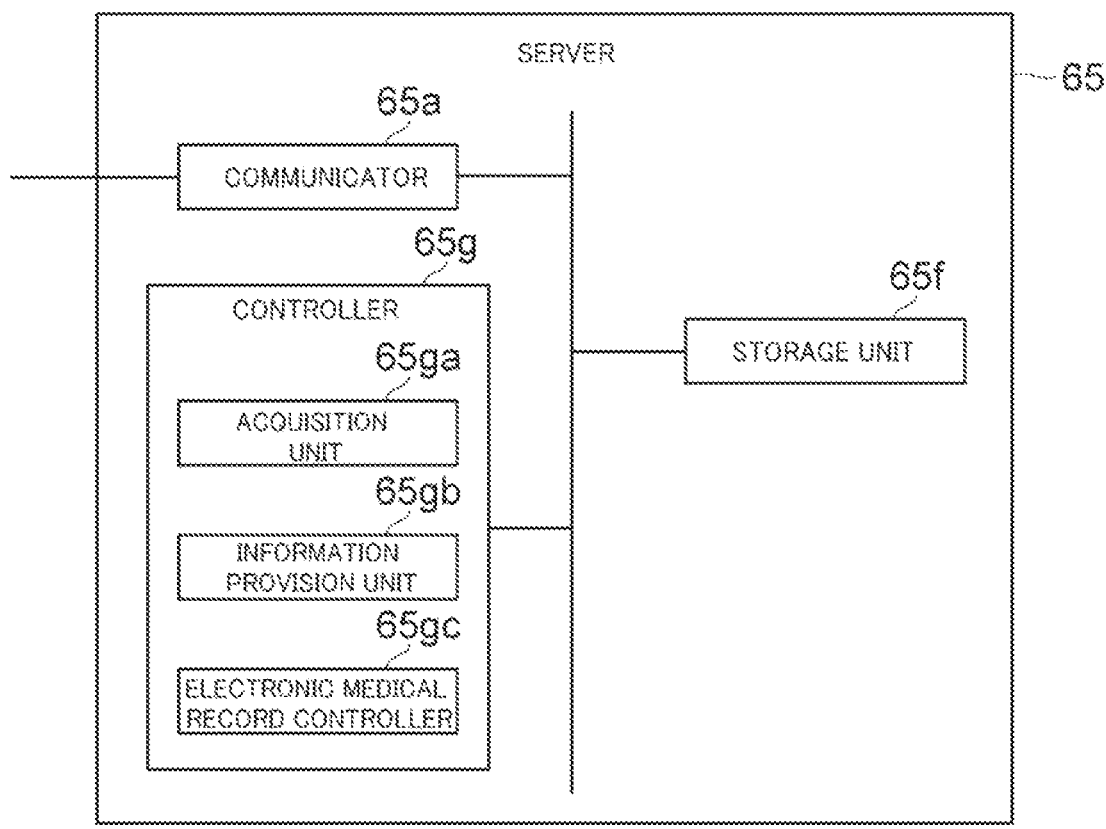
FIG. 15 is a pattern diagram showing an example of a part of a bed system according to an embodiment.

FIG. 15 is a pattern diagram showing an example of a part of a bed system according to an embodiment.

FIG. 15 is a block diagram of the server 65. As shown in FIG. 15, the server 65 includes, for example, a communicator 65a, a storage unit 65f, and a controller 65g (a processing unit). The controller 65g may include, for example, an acquisition unit 65ga, an information provision unit 65gb, an electronic medical record controller 65gc, and so on, for example.

The configuration described in relation to the communicator 60a can be applied to the communicator 65a. The configuration described in relation to the storage unit 60f can be applied to the storage unit 65f. The configuration described in relation to the controller 60g can be applied to the controller 65g. The controller 65g implements at least one of acquiring information from another device, providing information to another device, and controlling the electronic medical record storage unit 66, for example.

FIGS. 16(a) to 16(c) and FIGS. 17(a) to 17(c) are pattern diagrams showing examples of images displayed in a bed system according to an embodiment. These figures show examples relating to one of the plurality of images 61G displayed by the first display 61. As shown in the figures, one of the plurality of images 61G may display values of the information included in the vital signs information Ir2. The information included in the vital signs information Ir2 includes at least one of the blood pressure, the blood oxygen saturation, the blood glucose level, the heart rate, the pulse rate, the respiration rate, the weight, and the body temperature of the subject user, for example. In this example, a value Ira relating to the heart rate and a value Irb relating to the respiration rate are displayed as this information. In this example, the value Ira is "142". In this example, the value Irb is "21".

As the information included in the vital signs information I2 (the value Ira, the value Irb, and so on, for example), measurement values of the vital signs information I2 may be displayed in "real time", for example.

Figures 16A, 16B, 16C:
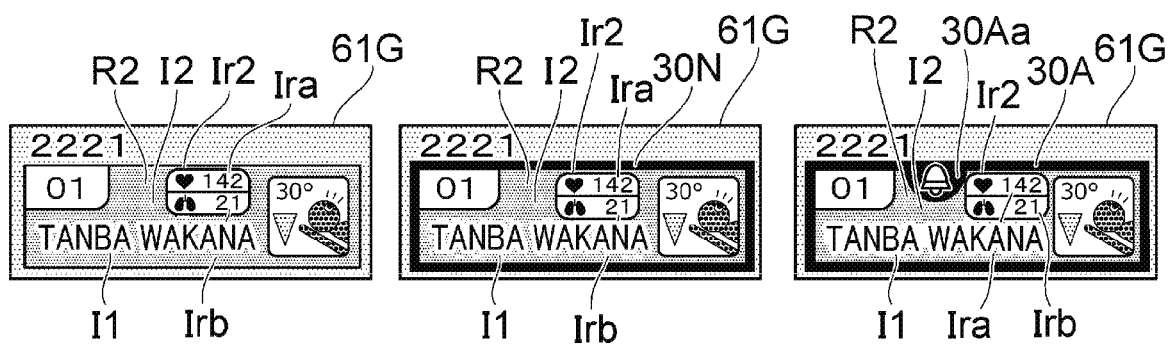
FIGS. 16(a) to 16(c) are pattern diagrams showing examples of images displayed in a bed system according to an embodiment.

FIG. 16(a) corresponds to a state in which no information is displayed in the third partial region R3. FIG. 16(b) corresponds to a state in which the notification display 30N is displayed in the third partial region R3. FIG. 16(c) corresponds to a state in which the warning display 30A is displayed in the third partial region R3.

Figures 17A, 17B, 17C:
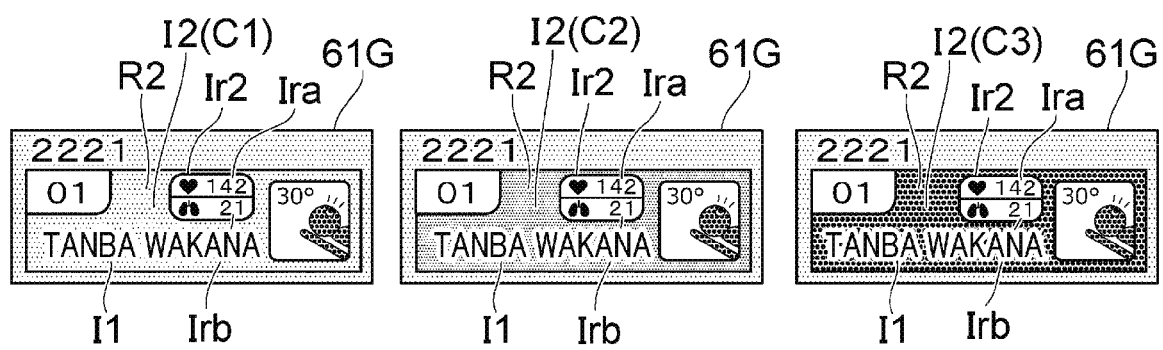
FIGS. 17(a) to 17(c) are pattern diagrams showing examples of images displayed in a bed system according to an embodiment.

In FIGS. 17(a) to 17(c), the vital signs information I2 is displayed according to color. In this example, the vital signs information I2 is displayed in three colors (a first color C1, a second color C2, and a third color C3). FIGS. 17(a) to 17(c) correspond respectively to the three colors.

Figure 18:
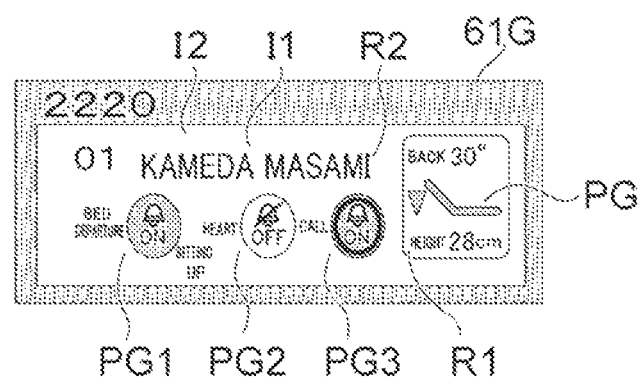
FIG. 18 is a pattern diagram showing an example of an image displayed in a bed system according to an embodiment.

FIG. 18 is a pattern diagram showing an example of an image displayed in a bed system according to an embodiment.

FIG. 18 shows an example relating to one of the plurality of images 61G displayed by the first display 61. As shown in FIG. 18, the pictogram PG is displayed in the first partial region R1. In this example, the state of the bed 51 is displayed as the pictogram PG. In this example, the back angle and the bed height are displayed. The knee angle and so on, for example, may also be displayed.

Furthermore, first to third pictograms PG1 to PG3 may be displayed in the second partial region R2 as an example of the vital signs information I2. The first pictogram PG1 includes information relating to at least one of bed departure, waking up, sitting up, and sitting on the edge of the bed, for example. The second pictogram PG2 includes information relating to the heart rate. The third pictogram PG3 includes information relating to the respiration rate.

The first pictogram PG1 may include information relating to a warning or notification setting (set or not set, ON/OFF) with respect to at least one of bed departure, waking up, sitting up, and sitting on the edge of the bed, for example. The second pictogram PG2 may include information relating to a warning or notification setting (set or not set, ON/OFF) with respect to the heart rate, for example. The third pictogram PG3 may include information relating to a warning or notification setting (set or not set, ON/OFF) with respect to the respiration rate, for example.

Figure 19:
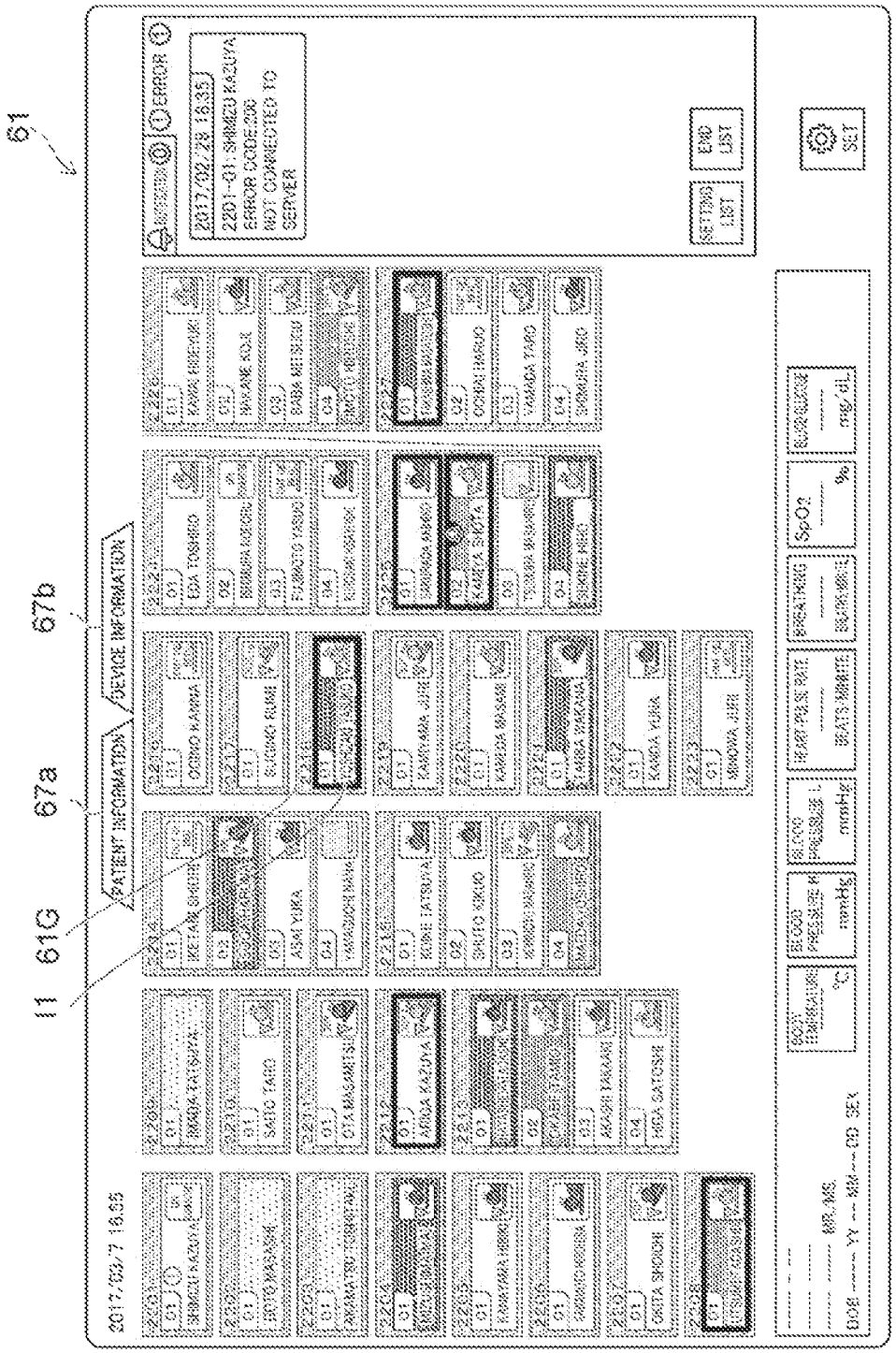
FIG. 19 is a pattern diagram showing an example of an image displayed in a bed system according to an embodiment.

FIG. 19 is a pattern diagram showing an example of an image displayed in a bed system according to an embodiment.

As shown in FIG. 19, a plurality of pages (a plurality of tabs) may be provided on the first display 61. In this example, a first page 67a and a second page 67b are provided. "Patient information" (or "user information"), for example, can be displayed on the first page 67a. "Device information", for example, can be displayed on the second page 67b. In the example shown in FIG. 19, the first page 67a has been selected. In this case, information relating to the respective users of the plurality of beds 51 is displayed.

When, on the other hand, the second page 67b is selected, the "device information", for example, is displayed. The "device information" includes information relating to various devices provided to the respective users of the plurality of beds 51. An example of the "device information" will be described below.

Figure 20A:
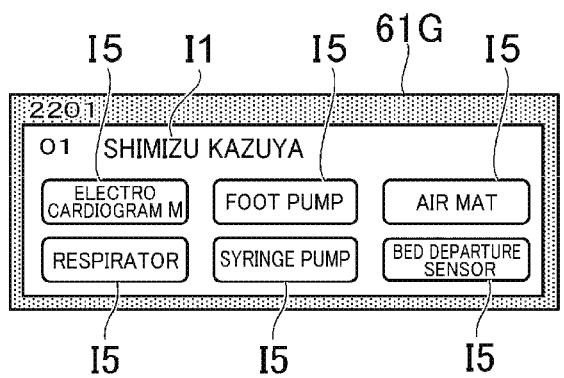
FIGS. 20(a) and 20(b) are pattern diagrams showing examples of images displayed in a bed system according to an embodiment.
Figure 20B:
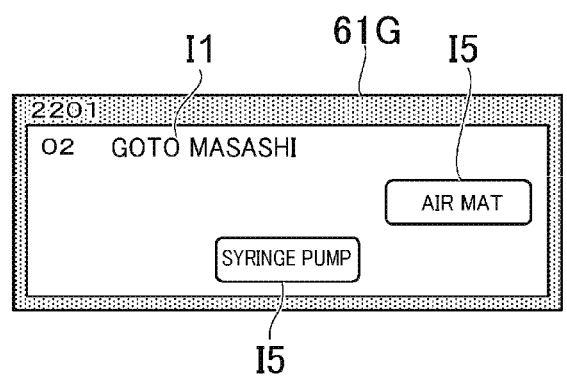

FIGS. 20(a) and 20(b) are pattern diagrams showing examples of images displayed in a bed system according to an embodiment.

These figures show one example of the plurality of images 61G (see FIG. 2) provided on the screen 61D of the first display 61 when the second page 67b has been selected. The plurality of images 61G correspond respectively to the users of the plurality of beds 51.

As shown in FIG. 20(a), device information I5 is displayed together with the identification information I1 (the name of the user, for example). The device information I5 is information relating to devices used by the corresponding user. In the example shown in FIG. 20(a), in the device information I5, an "electrocardiogram M", a "foot pump", an "air mat", a "respirator", a "syringe pump", and a "bed departure sensor" are used. In the example shown in FIG. 20(b), the "air mat" and the "respirator" are used.

The plurality of images 61G shown in FIGS. 20(a) and 20(b) are displayed on the single screen 61D in accordance with the plurality of beds 51.

By displaying information relating to the devices provided to the users of the plurality of beds 51, as in this example, the devices can be used effectively, for example. By viewing the second page 67b of the first display 61, a nurse or the like can identify all of the devices belonging to the plurality of beds 51 in a more easily understandable manner. Hence, a bed system having improved usability can be provided. For example, the positions of a limited number of devices can be ascertained easily.

As described below, the states of the plurality of beds 51 may also be displayed.

Figure 21A:
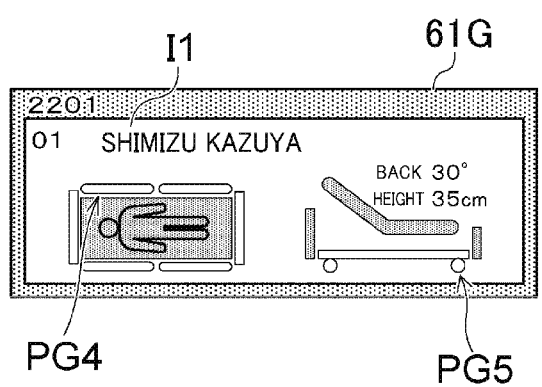
FIGS. 21(a) and 21(b) are pattern diagrams showing examples of images displayed in a bed system according to an embodiment.
Figure 21B:
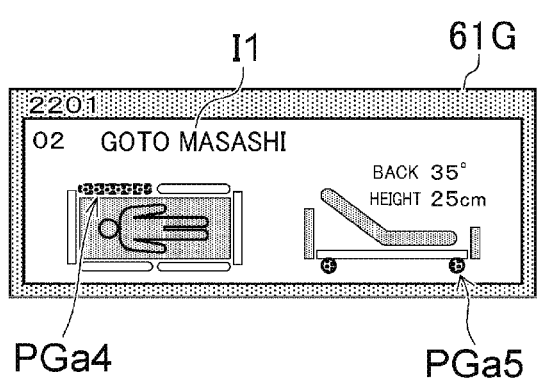

FIGS. 21(a) and 21(b) are pattern diagrams showing examples of images displayed in a bed system according to an embodiment.

These figures show examples relating to one of the plurality of images 61G. FIG. 21(a) corresponds to a situation in which the state of one of the plurality of beds 51 is normal. FIG. 21(b) corresponds to a situation in which the state of one of the plurality of beds 51 is abnormal. In this example, the state of the side rail and the locked state of casters are displayed.

In this example, as shown in FIG. 21(a), when the state of the side rail is normal and the casters are locked, a graphic PG4 corresponding to the side rail and a graphic PG5 corresponding to the casters are displayed.

As shown in FIG. 21(b), meanwhile, when a part of the side rail has been removed, for example, a graphic PGa4 corresponding to that part of the side rail is displayed. The graphic PGa4 is different to the graphic PG4 shown in FIG. 21(a). For example, the graphics have different colors. The images on these graphics may also flash, for example.

As shown in FIG. 21(b), for example, when the casters are unlocked, for example, a graphic PGa5 corresponding to the casters is displayed. The graphic PGa5 is different to the graphic PG5 shown in FIG. 21(a). For example, the graphics have different colors. The images on these graphics may also flash, for example.

The state of the bed 51 can be recognized in an easily understandable manner. As a result, a bed system having improved usability can be provided.

Figure 22:
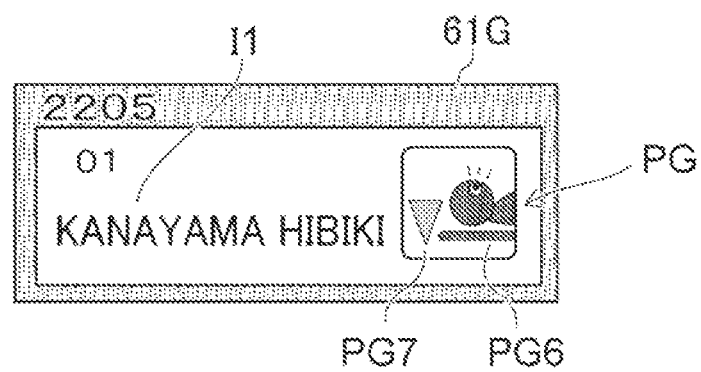
FIG. 22 is a pattern diagram showing an example of an image displayed in a bed system according to an embodiment.

FIG. 22 is a pattern diagram showing an example of an image displayed in a bed system according to an embodiment.

FIG. 22 shows an example relating to one of the plurality of images 61G. As shown in FIG. 22, the pictogram PG includes a graphic PG6 relating to the back section 70a and a graphic PG7 relating to the height of the bed 51 (the section), for example. The graphic PG6 indicates that the back section 70a is at a minimum (an angle of 0 degrees), for example. The graphic PG7 indicates that the height of the bed 51 is at a minimum. Thus, the pictogram PG may include various graphics indicating the state of the bed 51. As a result, the state of the bed 51 can be recognized in a more easily understandable manner.

An embodiment may include the following configurations (concepts, for example).

(Configuration 1)

A bed system including:

an acquisition unit for acquiring a plurality of user interface device information from a plurality of user interface devices; and a first display for displaying a plurality of images corresponding respectively to the plurality of user interface devices on a single screen on the basis of the plurality of user interface device information acquired by the acquisition unit, wherein one set of the plurality of user interface device information includes state information including at least one of bed state information relating to the state of one bed among a plurality of beds and user state information relating to the state of a user of the one bed among the plurality of beds, one image among the plurality of images includes a state display corresponding to the state information, and when the state information is abnormal, the first display displays a warning display on the one image among the plurality of images.

(Configuration 2)

The bed system according to configuration 1, wherein the bed state information includes bed moving part information relating to at least one of a height and an angle of the one bed among the plurality of beds, the user state information includes at least one of vital signs information relating to the user and user behavior information relating to the user, the vital signs information includes information relating to at least one of a blood pressure, a blood oxygen saturation, a blood glucose level, a heart rate, a pulse rate, a respiration rate, a weight, and a body temperature of the user, and the user behavior information includes information relating to at least one of bed departure, sleeping, waking up, sitting up, and sitting on the edge of the bed in relation to the user.

(Configuration 3)

The bed system according to configuration 2, wherein each of the plurality of images includes a first partial region, a second partial region, and a third partial region, at least a part of the second partial region being positioned between the first partial region and the third partial region, the first display displays a pictogram including the state display in the first partial region, the first display displays identification information specifying the user in at least a part of the second partial region, and the first display displays the warning display in the third partial region.

(Configuration 4)

The bed system according to configuration 3, wherein the first display displays the vital signs information in at least a part of the second partial region.

(Configuration 5)

The bed system according to configuration 3 or 4, wherein the first display displays the warning display in the third partial region when at least one of the bed departure state of the user, the waking-up state of the user, the sitting-up state of the user, the sitting-on-the-edge-of-the-bed state of the user, the heart rate of the user, and the respiration rate of the user is abnormal.

(Configuration 6)

The bed system according to any one of configurations 3 to 5, wherein the first display displays the warning display in the third partial region when the bed state information is abnormal.

(Configuration 7)

The bed system according to any one of configurations 3 to 6, wherein the third partial region is positioned on the periphery of the first partial region and the second partial region.

(Configuration 8)

The bed system according to any one of configurations 3 to 7, wherein the first display further displays a notification display in the third partial region when at least one of the heart rate of the user and the respiration rate of the user varies beyond a reference, and the heart rate of the user and the respiration rate of the user are acquired from the one bed among the plurality of beds or an auxiliary device of the one bed among the plurality of beds.

(Configuration 9)

The bed system according to configuration 8, wherein the warning display has at least one of a larger surface area than a surface area of the notification display and a different pattern to a pattern included in the notification display.

(Configuration 10)

The bed system according to configuration 8 or 9, wherein a chroma of the notification display is higher than a chroma of the display of the vital signs information.

(Configuration 11)

The bed system according to configuration 8 or 9, wherein an absolute value of a difference between a hue of the notification display and a hue of red is smaller than an absolute value of a difference between a hue of the display of the vital signs information and the hue of red.

(Configuration 12)

The bed system according to any one of configurations 3 to 11, wherein a chroma of the warning display is higher than a chroma of the display of the vital signs information.

(Configuration 13)

The bed system according to configuration 3 or 4, wherein an absolute value of a difference between a hue of the warning display and a hue of red is smaller than an absolute value of a difference between a hue of the display of the vital signs information and the hue of red.

(Configuration 14)

The bed system according to any one of configurations 3 to 8, wherein the identification information includes character information, and the vital signs information is displayed according to a color on the periphery of the identification information.

(Configuration 15)

The bed system according to configuration 14, wherein the color includes a first color indicating normal, a second color indicating caution, and a third color indicating a warning, a chroma of the third color is higher than a chroma of the second color, and the chroma of the second color is higher than a chroma of the first color.

(Configuration 16)

The bed system according to configuration 14, wherein the plurality of colors include a first color indicating normal, a second color indicating caution, and a third color indicating a warning, and an absolute value of a difference between a hue of the third color and a hue of red is smaller than an absolute value of a difference between a hue of the second color and the hue of red.

(Configuration 17)

The bed system according to configuration 16, wherein the absolute value of the difference between the hue of the second color and the hue of red is smaller than an absolute value of a difference between a hue of the first color and the hue of red.

(Configuration 18)

The bed system according to any one of configurations 3 to 17, wherein a surface area of the second partial region is larger than a surface area of the first partial region.

(Configuration 19)

The bed system according to any one of configurations 3 to 18, wherein the warning display includes red.

(Configuration 20)

The bed system according to any one of configurations 3 to 19, wherein the warning display includes flashing.

(Configuration 21)

The bed system according to any one of configurations 3 to 20, wherein each of the plurality of images further includes an outer edge partial region on the periphery of the first partial region, the second partial region, and the third partial region.

(Configuration 22)

The bed system according to any one of configurations 1 to 21, wherein, when one image among the plurality of images receives input, the first display displays information corresponding to the one image among the plurality of images.

(Configuration 23)

The bed system according to configuration 22, wherein the information corresponding to the one image among the plurality of images is displayed in a part of the single screen.

(Configuration 24)

The bed system according to any one of configurations 1 to 23, further including the plurality of beds, wherein the plurality of user interface devices are connected respectively to the plurality of beds.

(Configuration 25)

The bed system according to any one of configurations 1 to 24, wherein the first display is capable of displaying information relating to states of devices corresponding respectively to the plurality of user interface devices.

According to this embodiment, a bed system having improved usability can be provided.

Embodiments of the present invention were described above with reference to specific examples. However, the present invention is not limited to these specific examples. For example, a person skilled in the art could implement the present invention similarly by selecting appropriate, well-known configurations as specific configurations of the respective elements, such as the acquisition unit and the first display, included in the bed system, and as long as similar effects are obtained as a result, these configurations are included in the scope of the present invention.

Components obtained by combining two or more elements of the specific examples within a technically feasible scope are also included within the scope of the present invention, provided these components encompass the gist of the present invention.

In addition, all bed systems that could be realized by a person skilled in the art by implementing appropriate design modifications on the basis of the bed system described above as an embodiment of the present invention are likewise included in the scope of the present invention, provided these bed systems encompass the gist of the present invention.

Furthermore, a person skilled in the art could arrive at various modified and amended examples within the scope of the spirit of the present invention, and these modified and amended examples are also included within the scope of the present invention.

REFERENCE SIGNS LIST

11 Height display pattern
12 Angle display pattern
13 Angle display characters
14 User behavior display
30A Warning display
30Aa Distinctively shaped pattern
30N Notification display
50 Bed device
50a Communicator
50b User interface device
50c Display
50d Short-range communicator
50e Output device
50ea Speaker
50eb Lighting device
50f Storage unit
50g Controller
51, 51A to 51C Bed
51i Bed moving part information
51iD Bed moving part display
52, 52A to 52C Auxiliary device
52i User behavior information
53, 53A to 53C Measurement device
53a Blood pressure gauge
53b Pulse oximeter
53c Thermometer
53d Blood glucose meter
53i Measurement information
55, 55A to 55C User interface device
55i, 55iA to 55iC User interface device information
60 Input/output device
60a Communicator
60b User interface device
60c Display
60d Short-range communicator
60e Output device
60ea Speaker
60eb Lighting device
60f Storage unit
60g Controller
61 First display
61D Screen
61G Image
61H Window region
61I Acquisition unit
61M Message region
62 Second display
62a Communicator
62b User interface device
62c Display
62d Short-range communicator
62e Output device
62ea Speaker
62eb Lighting device
62f Storage unit
62g Controller
65 Server
65a Communicator
65f Storage unit
65g Controller
65ga Acquisition unit
65gb Information provision unit
65gc Electronic medical record controller
66 Electronic medical record storage unit
67a, 67b First and second pages
70 Moving part
70a Back section
70b Knee section
70c Leg section
70d Height modifying part
110 Bed system
C1 to C6 First to sixth colors
I1 Identification information
I2 Vital signs information
I3 Ward number
I4 Number
I5 Device information
Ira, Irb Value
L1 to L3 Length
PG Pictogram
PG1 to PG3 First to third pictograms
PG4 to PG7 Graphic
PGa4, PGa5 Graphic
R1 to R3 First to third partial regions
R4 Outer edge partial region
R5 Background region
W1 to W3 Length

The invention claimed is:

1. A bed system comprising:
a receiver configured to receive a bed height status indicating whether a height of a bed is low status, an angle of the bed, and a first user status indicating whether a first user is sleeping; and
a first display configured to display a single pictogram including the bed height status, the angle of the bed, and the first user status, the single pictogram indicating a current status related to the bed height status, the angle of the bed, and the first user status excluding a past status related to the bed height status, the angle of the bed, and the first user status.

2. The bed system according to claim 1, wherein if the receiver is configured to receive the bed height status of the first user and a second user, the angles of the bed of the first user and the second user, the first user status, and a second user status, the first display is configured to display both a first single pictogram based on the bed height status of the first user, the angle of the bed of the first user, and the first user status and a second single pictogram based on the bed height status of the second user, the angle of the bed of the second user, and the second user status on a single screen.

3. The bed system according to claim 2, wherein the first display is configured to display a first image for the first user and a second image for the second user, each the first image and the second image including the single pictogram.

4. The bed system according to claim 3, wherein the image includes a first partial region, a second partial region, and a third partial region, at least a part of the second partial region being positioned between the first partial region and the third partial region,
the first display displays the single pictogram in the first partial region,
the first display displays identification information specifying the first user or the second user in at least a part of the second partial region, and
the first display displays a warning display in the third partial region.

5. The bed system according to claim 1, wherein the single pictogram includes an angle display pattern and an angle display character.

6. The bed system according to claim 1, wherein the first display is configured to display an image for the first user, the image including the single pictogram.

7. The bed system according to claim 6, wherein the image includes a first partial region, a second partial region, and a third partial region, at least a part of the second partial region being positioned between the first partial region and the third partial region,
   the first display displays the single pictogram in the first partial region,
   the first display displays identification information specifying the first user in at least a part of the second partial region, and
   the first display displays a warning display in the third partial region.

8. The bed system according to claim 7, wherein the first display displays a vital signs information in at least a part of the second partial region.

9. The bed system according to claim 7, wherein the first display displays the warning display in the third partial region in the image if a heart rate of the first user or a respiration rate of the first user is abnormal.

10. The bed system according to claim 7, wherein the third partial region is positioned on a periphery of the first partial region and the second partial region.

11. The bed system according to claim 7, wherein the first display further displays a notification display in the third partial region of the image if at least one of a heart rate of the first user and a respiration rate of the first user varies beyond a threshold reference.

12. The bed system according to claim 1, wherein the receiver is configured to receive a vital signs information that includes information relating to at least one of a blood pressure, a blood oxygen saturation, a blood glucose level, a heart rate, a pulse rate, a respiration rate, a weight, and a body temperature of the first user.

13. The bed system according to claim 1, further comprising:
   a sensor configured to detect the first user status using a biological information of the first user, the sensor being located between the bed and a mattress.

* * * * *